(12) United States Patent
Peschle et al.

(10) Patent No.: US 6,586,192 B1
(45) Date of Patent: Jul. 1, 2003

(54) COMPOSITIONS AND METHODS FOR USE IN AFFECTING HEMATOPOIETIC STEM CELL POPULATIONS IN MAMMALS

(75) Inventors: Cesare Peschle, Rome (IT); Benedikt L. Ziegler, Tuebingen (DE)

(73) Assignees: Thomas Jefferson University, Philadelphia, PA (US); Instituto Superiore di Sanita, Rome (IT)

(*) Notice: Subject to any disclaimer, the term of this patent is extended or adjusted under 35 U.S.C. 154(b) by 0 days.

(21) Appl. No.: 09/322,352

(22) Filed: May 28, 1999

Related U.S. Application Data
(60) Provisional application No. 60/087,153, filed on May 29, 1998.

(51) Int. Cl.$^7$ ............... G01N 33/567; G01N 33/566; C12N 5/00; C12N 5/08; C07K 1/00
(52) U.S. Cl. .............. 435/7.21; 435/325; 435/366; 435/372; 436/501; 436/503; 530/351
(58) Field of Search .............. 435/7.21, 325, 435/366, 372; 436/501, 503; 530/351

(56) References Cited

U.S. PATENT DOCUMENTS

| | | | |
|---|---|---|---|
| 5,023,243 A | 6/1991 | Tullis | |
| 5,034,506 A | 7/1991 | Summerton et al. | |
| 5,168,053 A | 12/1992 | Altman | |
| 5,190,931 A | 3/1993 | Inoue | |
| 5,747,651 A | 5/1998 | Lemischka | |
| 5,851,999 A | 12/1998 | Ullrich et al. | |
| 5,912,133 A | 6/1999 | Lemischka | |

FOREIGN PATENT DOCUMENTS

| | | |
|---|---|---|
| WO | WO94/17810 | 8/1994 |
| WO | WO94/23744 | 10/1994 |

OTHER PUBLICATIONS

Sato et al., 1999, Blood, 94:2548–2554.
Almeida–Porada et al., 1998, Exp. Hematol. 26:749.
Applebaum et al., 1992, Blood 80:1608–1613.
Ashara et al., 1997, Science 275:964–967.
Bensinger et al., 1996, Blood 88:4132–4138.
Berenson et al., 1991, Blood 77:1717–1722.
Berenson et al., J. Clin. Invest. 81:951–955.
Bhatia et al., 1998, Nature Med.4:1038–1045.
Bhatia et al., 1997, Proc. Natl. Acad. Sci. U.S.A. 94:5320–5325.
Bird et al., 1988, Science 242:423–426.
Bock et al., 1995, J. Exp. Med. 182:2037–2043.
Brandt et al., 1990, J. Clin. Invest. 86:932–941.
Breems et al., 1996, Blood 87:5370–5378.
Carè et al., 1999, Oncogene 18:1993–2001.
Cech et al., 1992, J. Biol. Chem. 267:17479–17482.
Conneally et al., 1997, Proc. Natl. Acad. Sci. U.S.A. 94:9836–9841.
Cech, 1988, J. Amer. Med. Assn. 260:3030.
Choi et al., 1998, Development 125:725–732.
Civin et al., 1996, Blood 88:4102–4109.
Cranage et al., 1986, EMBO J. 5:3057–3063.
Ferrari et al., 1998, Science 279:1528–1530.
Flamme et al., 1992, Development 116:435–439.
Gabbianelli et al., 1995, Blood 86:1661–1670.
Gabbianelli et al., 1990, Science 249:1561–1564.
Gabrilovich et al.,1998, Blood 92:4150–4166.
Garcia–Ojeda et al., 1998, J. Exp. Med. 187:1813–1823.
Goodell et al., 1996, J. Exp. Med. 183:1797–1806.
Guerriero et al., 1995, Blood 86:3725–3736.
Hampel et al., 1989, Biochemistry 28;4929–4933.
Hao et al., 1996, Blood 88:3306–3313.
Huston et al.,1988, Proc. Natl. Acad. Sci. U.S.A. 85:5879–5883.
Johnson et al., 1996, Blood 88:629a.
Kabrun et al., 1997, Development 124:2039–2048.
Katoh et al., 1995, Cancer Res. 55:5687–5692.
Kawashim, et al., 1996, Blood 87:4136–4142.
Kay et al., 1994, T.I.G. 10:253–257.
Kennedy et al., 1997, Nature 386:488–492.
Labbaye et al., 1995, J. Clin. Invest. 95:2346–2358.
Larochelle et al., 1996, Nature Med. 2:1329–1337.
Matthews et al., 1991, Proc. Natl. Acad. Sci. USA 88:9026–9030.
Marcus–Sakura, 1988, Anal. Biochem. 172:289.
Miraglia et al., 1997, Blood 90:5013–5021.
Morrison et al., 1997, Cell 88:287–298.
Nielson et al., 1991, Science 254:1497.
Nishikawa et al., 1998, Development 125;1747–1757.
Nolta et al., 1994, Blood 83:3041–3047.
Ogawa et al., 1993, Blood 81:2844–2853.
Orlic and Bodine, 1994, Blood 84:3991–3994.
Osawa et al., 1996, Science 273:242–245.
Petersen et al., 1999, Science 284:1168–1170.
Ogawa et al., 1993, Science 259:1896–1899.
Pittenger et al., 1999, Science 284:143–147.
Risau et al., 1995, Ann. Rev. Cell. Dev. Biol. 11:73–91.
Shalaby et al., 1995, Nature 376:62–66.
Shalaby et al., 1997, Cell 89:981–990.
Sutherland et al., 1990, Proc. Natl. Acad. Sci. U.S.A. 87:3584–3588.
Sutherland et al., 1996, Exp. Hematol. 24:795–806.
Terman et al., 1991, Oncogene 6:1677–1683.
Testa et al., 1996, Blood 88:3391–3406.
Uchida et al., 1996, Blood 88:1297–1305.
Valtieri et al., 1994, Cancer Res. 54:4398–4404.
van der Loo and Ploemacher, 1995, Blood 85:2598–2606.

(List continued on next page.)

*Primary Examiner*—Christina Chan
*Assistant Examiner*—Michail A Belyavskyi
(74) *Attorney, Agent, or Firm*—Akin Gump Strauss Hauer & Feld, L.L.P.

(57) ABSTRACT

The invention relates to a methods of obtaining and expanding a purified population of long-term repopulating hematopoietic stem cells. The invention also relates to the uses of a purified population of long-term repopulating hematopoietic stem cells.

59 Claims, 10 Drawing Sheets

OTHER PUBLICATIONS

Verma et al., 1997, Nature 389:239–242.
Verstegen et al., 1998, Blood 91;1966–1976.
Wang et al., 1997, Blood 89:3919–3924.
Warburton et al., 1991, Genomics 11:324–333.
Weintraub, 1990, Scientific American 262:40.
Yin et al., 1997, Blood 90:5002–5012.
Zanjani et al., 1996, Int. J. Hematol. 63:179–192.
Zanjani et al., 1998, Blood (Suppl. I) 92:504.
Zanjani et al., 1998, Exp. Hematol. 26:353–360.
Ziegler et al., 1999, Blood 93:3355–3368.

SEQUENCE LISTING

<160> NUMBER OF SEQ ID NOS: 10

<210> SEQ ID NO 1
<211> LENGTH: 22
<212> TYPE: DNA
<213> ORGANISM: artificial sequence
<220> FEATURE:
<223> OTHER INFORMATION: KDR Primer

<400> SEQUENCE: 1
aaaacctttt gttgcttttt ga                                        22

<210> SEQ ID NO 2
<211> LENGTH: 22
<212> TYPE: DNA
<213> ORGANISM: artificial sequence
<220> FEATURE:
<223> OTHER INFORMATION: KDR Primer

<400> SEQUENCE: 2
gaaatgggat tggtaaggat ga                                        22

```
<210> SEQ ID NO 3
<211> LENGTH: 22
<212> TYPE: DNA
<213> ORGANISM: artificial sequence
<220> FEATURE:
<223> OTHER INFORMATION: VEGFRI/Flt1 Primer

<400> SEQUENCE: 3
aaaccaagac tagatagcgt ca                                          22

<210> SEQ ID NO 4
<211> LENGTH: 22
<212> TYPE: DNA
<213> ORGANISM: artificial sequence
<220> FEATURE:
<223> OTHER INFORMATION: VEGFRI/Flt1 Primer

<400> SEQUENCE: 4
ttctcacata atcggggttc tt                                          22

<210> SEQ ID NO 5
<211> LENGTH: 22
<212> TYPE: DNA
<213> ORGANISM: artificial sequence
<220> FEATURE:
<223> OTHER INFORMATION: VEGFRII/Flt4 Primer

<400> SEQUENCE: 5
gacaaggagt gtgaccactg aa                                          22

<210> SEQ ID NO 6
<211> LENGTH: 22
<212> TYPE: DNA
<213> ORGANISM: artificial sequence
<220> FEATURE:
<223> OTHER INFORMATION: VEGFRII/Flt4 Primer

<400> SEQUENCE: 6
tgaagggaca ttgtgtgaga ag                                          22

<210> SEQ ID NO 7
<211> LENGTH: 24
<212> TYPE: DNA
<213> ORGANISM: artificial sequence
<220> FEATURE:
<223> OTHER INFORMATION: Tie1 Primer

<400> SEQUENCE: 7
gagtccttct ttgggagata gtga                                        24

<210> SEQ ID NO 8
<211> LENGTH: 24
<212> TYPE: DNA
<213> ORGANISM: artificial sequence
<220> FEATURE:
<223> OTHER INFORMATION: Tie1 Primer

<400> SEQUENCE: 8
gtcagactgg tcacaggtta gaca                                        24

<210> SEQ ID NO 9
<211> LENGTH: 24
<212> TYPE: DNA
<213> ORGANISM: artificial sequence
<220> FEATURE:
<223> OTHER INFORMATION: Tek Primer
```

-continued

```
<400> SEQUENCE: 9 cattttttgca gagaacaaca tagg                                              24

<210> SEQ ID NO 10
<211> LENGTH: 24
<212> TYPE: DNA
<213> ORGANISM: artificial sequence
<220> FEATURE:
<223> OTHER INFORMATION: Tek Primer

<400> SEQUENCE: 10
tcaagcactg gataaattgt agga                                               24
```

COMPOSITIONS AND METHODS FOR USE IN AFFECTING HEMATOPOIETIC STEM CELL POPULATIONS IN MAMMALS

CROSS-REFERENCE TO RELATED APPLICATIONS

This application claims priority, under 35 U.S.C. §119(e), to U.S. Provisional Application No. 60/087,153, filed on May 29, 1998, which is hereby incorporated herein by reference in its entirety.

BACKGROUND OF THE INVENTION

Hematopoiesis in mammals is maintained by a pool of self-renewing hematopoietic stem cells (HSCs) (Ogawa, 1993, Blood 81:2844–2853). HSCs feed into lineage(s)-committed undifferentiated hematopoietic progenitor cells (HPCs) with little or no self-renewal capacity (Ogawa, 1993, Blood 81:2844–2853). The HPCs in turn generate morphologically recognizable differentiated precursors and terminal cells circulating in peripheral blood.

Human HSCs are identified on the basis of their capacity for long-term hematopoietic repopulation in vitro and in vivo. Specifically, in vitro repopulation of an irradiated allogeneic stromal adherent layer in long term culture (LTC) of Dexter type has been observed. In Dexter type LTC, primitive HPCs and HSCs are assessed as five to eight week and twelve week LTC initiating cells (LTC-ICs; Sutherland et al., 1990, Proc. Natl. Acad. Sci. U.S.A. 87:3584–3588; Valtieri et al., 1994, Cancer Res. 54:4398–4404; Hao et al., 1996, Blood 88:3306–3313), or cobblestone area forming cells (CAFCs; Breems et al., 1996, Blood 87:5370–5378). Particularly, short term repopulating primitive HPCs have been identified in five to eight week LTC (Sutherland et al., 1990, Proc. Natl. Acad. Sci. U.S.A. 87:3584–3588; Larochelle et al., 1996, Nature Med. 2:1329–1337), whereas long-term repopulating putative HSCs have been identified in twelve week LTC (Hao et al., 1996, Blood 88:3306–3313). Moreover, in vivo repopulation of severe combined immunodeficiency (SCID) mice at two months (Nolta et al., 1994, Blood 83:3041–3047) or non-obese diabetic SCID (SCID-NOD) mice at one and a half months (Bock et al., 1995, J. Exp. Med. 182:2037–2043) after irradiation and HSC injection has been observed.

In murine embryonic life (day 7.5 of gestation), a close developmental association of the hematopoietic and endothelial lineages takes place in the yolk sack blood islands, leading to the hypothesis that the two lineages share a common ancestor referred to as the hemoangioblast (Flamme et al., 1992, Development 116:435–439; Risau et al., 1995, Ann. Rev. Cell. Dev. Biol. 11:73–91).

Vascular endothelial growth factor (VEGF) and one of its receptors, VEGFRII termed Flk1 in mice and KDR in humans, play a key role in early hemoangiogenesis. In fact, Flk1$^-$ knock-out mice are unable to form blood islands and blood vessels (Shalaby et al., 1995, Nature 376:62–66). Differentiated murine embryonic stem cells treated with VEGF and the ligand for c-kit receptor at the embryoid stage give rise to primitive blast cells which generate the various hematopoietic lineages (Kennedy et al., 1997, Nature 386:488–492; Kabrun et al., 1997, Development 124:2039–2048): these data suggest a role for VEGF at the level of primitive HPCs in murine embryonic hematopoiesis. There are no data concerning the effect of expression or the function of KDR in human embryonic/fetal HSCs.

In post-fetal life, the VEGF/KDR system plays an important role in the endothelial lineage. Indeed, KDR and CD34 antigens are expressed on progenitors of human adult endothelial cells (Ashara et al., 1997, Science 275:964–967). Again, there are no data concerning the effect of expression or the function of KDR in human post-fetal HSCs, particularly long-term repopulating HSCs. Most studies have focused on examination of the effect of VEGF on partially purified HPCs. The results of these studies suggest that VEGF exerts an enhancing or inhibitory effect on bone marrow (BM) HPC colony formation stimulated by diverse hematopoietic growth factors (HGFs; Broxmeyer et al., 1995, Int. J. Hematol. 62:203–215) and a stimulatory effect on hematopoietic cells in normal mice (Gabrilovich et al., 1998, Blood 92:4150–4166). In addition, KDR mRNA is expressed in cord blood (CB) and BM partially purified HPCs, while VEGF does not affect CB HPC colony formation but exerts an anti-apoptotic action on irradiated HPCs (Katoh et al., 1995, Cancer Res. 55:5687–5692).

There is a need in the art for efficient methods of purifying and characterizing long term repopulating HSCs and for methods of ex vivo expansion of these cells. In addition, there is a need in the art for methods of treating a variety of diseases using HSCs. The present invention satisfies these needs.

BRIEF SUMMARY OF THE INVENTION

The invention includes a method of obtaining a cell population enriched for long-term repopulating human hematopoietic stem cells. The method comprises obtaining a population of cells from human hematopoietic tissue and isolating a population of KDR$^+$ cells therefrom, thereby obtaining a cell population enriched for long-term repopulating human hematopoietic stem cells.

In one aspect, the human hematopoietic tissue is selected from the group consisting of embryonic hematopoietic tissue, fetal hematopoietic tissue, and post-natal henlatopoietic tissue.

In another aspect, the embryonic hematopoietic tissue is selected from the group consisting of yolk sac, and embryonic liver.

In yet another aspect, the fetal hematopoietic tissue is selected from the group consisting of fetal liver, fetal bone marrow and fetal peripheral blood.

In a further aspect, the post-natal hematopoietic tissue is selected from the group consisting of cord blood, bone marrow, normal peripheral blood, mobilized peripheral blood, hepatic hematopoietic tissue, and splenic hematopoietic tissue.

In yet a further aspect, the KDR$^+$ cells are isolated using a reagent which specifically binds KDR.

In one aspect, the reagent is an antibody is selected from the group consisting of a polyclonal antibody and a monoclonal antibody.

In another aspect, the antibody is a monoclonal antibody.

In yet another aspect, the monoclonal antibody is 260.4. In a further aspect, the KDR$^+$ cells are isolated using a conjugated vascular endothelial growth factor or a molecule derived therefrom.

In yet a further aspect, the cells are starvation resistant long-term repopulating human hematopoietic stem cells.

The invention includes an enriched population of long-term repopulating human hematopoietic stem cells obtained using a method of obtaining a cell population enriched for long-term repopulating human hematopoietic stem cells. The method comprises obtaining a population of cells from human hematopoietic tissue and isolating a population of KDR⁺ cells therefrom, thereby obtaining a cell population enriched for long-term repopulating human hematopoietic stem cells. The invention also includes a cell isolated using this method. The invention also includes the cell isolated using this method wherein the cell comprises an isolated nucleic acid.

In one aspect, the cell comprising an isolated nucleic acid comprises an isolated nucleic acid selected from the group consisting of a nucleic acid encoding adenosine deamininase, a nucleic acid encoding β-globin, a nucleic acid encoding multiple drug resistance, an antisense nucleic acid complementary to a human immunodeficiency virus nucleic acid, an antisense nucleic acid complementary to a nucleic acid encoding a cell cycle gene, and an antisense nucleic acid complementary to a nucleic acid encoding an oncogene.

In another aspect, the isolated nucleic acid is operably linked to a promoter/regulatory sequence.

In even another aspect, the promoter/regulatory sequence is selected from the group consisting of a retroviral long terminal repeat, and the cytomegalovirus immediate early promoter.

The invention includes a method of obtaining a purified population of long-term repopulating human hematopoietic stem cells. The method comprises obtaining a population of cells from human hematopoietic tissue, isolating a population of hematopoietic progenitor cells therefrom, and isolating a population of KDR⁺ cells from the population of hematopoietic progenitor cells, thereby obtaining a purified population of long-term repopulating human hematopoietic stem cells.

In one aspect, the human hematopoietic tissue is selected from the group consisting of embryonic hematopoietic tissue, fetal hematopoietic tissue, and post-natal heniatopoietic tissue.

In another aspect, the embryonic hematopoietic tissue is selected from the group consisting of yolk sac, and embryonic liver.

In yet another aspect, the fetal hematopoietic tissue is selected from the group consisting of fetal liver, fetal bone marrow and fetal peripheral blood.

In a further aspect, the post-natal hematopoietic tissue is selected from the group consisting of cord blood, bone marrow, normal peripheral blood, mobilized peripheral blood, hepatic hematopoietic tissue, and splenic hematopoietic tissue.

In yet a further aspect, the hematopoietic progenitor cells are isolated using at least one method selected from the group consisting of isolation of cells expressing an early marker using antibodies specific for said marker, isolation of cells not expressing a late marker using antibodies specific for said late marker, isolation of cells based on a physical property of said cells, and isolation of cells based on a biochemical/biological property of said cells.

In another aspect, the early marker is selected from the group consisting of CD34, Thy-1, c-kit receptor, flt3 receptor, AC133, vascular endothelial growth factor receptor I, vascular endothelial growth factor receptor III, Tie1, Tek, and basic fibroblast growth factor receptor.

In yet another aspect, the late marker is a lineage (lin) marker.

In a further aspect, the early marker is CD34.

In even a further aspect, the hematopoietic progenitor cells are obtained from the hematopoietic tissue using an antibody which specifically binds CD34 to select a population of CD34⁺ hematopoietic progenitor cells.

In another aspect, the population of KDR⁺ cells is isolated from the population of CD34⁺ hematopoietic progenitor cells using an antibody which specifically binds KDR.

In yet another aspect, the antibody is selected from the group consisting of a polyclonal antibody and a monoclonal antibody.

In even yet another aspect, the antibody is a monoclonal antibody.

In a further aspect, the monoclonal antibody is 260.4.

In even a further aspect, the cells are starvation resistant human hematopoietic stem cells.

The invention includes an isolated purified population of long-term repopulating human hematopoietic stem cells obtained by a method of obtaining a purified population of long-term repopulating human hematopoietic stem cells. The method comprises obtaining a population of cells from human hematopoietic tissue, isolating a population of hematopoietic progenitor cells therefrom, and isolating a population of KDR⁺ cells from the population of hematopoietic progenitor cells, thereby obtaining a purified population of long-term repopulating human hematopoietic stem cells. The invention also includes a cell obtained by this method. The invention further includes a cell obtained by this method wherein the cell comprises an isolated nucleic acid.

The one aspect, the isolated nucleic acid is selected from the group consisting of a nucleic acid encoding adenosine deaminase, a nucleic acid encoding β-globin, a nucleic acid encoding multiple drug resistance, an antisense nucleic acid complementary to a human immunodeficiency virus nucleic acid, an antisense nucleic acid complementary to a nucleic acid encoding a cell cycle gene, and an antisense nucleic acid complementary to a nucleic acid encoding an oncogene.

In another aspect, the isolated nucleic acid is operably linked to a promoter/regulatory sequence.

In yet another aspect, the promoter/regulatory sequence is selected from the group consisting of a retroviral long terminal repeat, and the cytomegalovirus immediate early promoter.

In a further aspect, the hematopoietic progenitor cells are obtained from said hematopoietic tissue using antibody which specifically binds CD34 to select a population of CD34⁻ cells.

In an even further aspect, the hematopoietic progenitor cells are obtained from said population of CD34⁻ cells using antibody which specifically binds lin to select a population of CD34⁻lin⁻ cells.

In another aspect, the population of KDR⁺ cells is isolated from the population of CD34⁻lin⁻ cells using an antibody which specifically binds KDR.

In yet another aspect, the antibody is selected from the group consisting of a polyclonal antibody and a monoclonal antibody.

In even another aspect, the antibody is a monoclonal antibody.

In a further aspect, the monoclonal antibody is 260.4.

The invention includes an isolated purified population of long-term repopulating human hematopoietic stem cells obtained by a method of obtaining a purified population of long-term repopulating human hematopoietic stem cells. The method comprises obtaining a population of cells from human hematopoietic tissue, isolating a population of hematopoietic progenitor cells therefrom, and isolating a population of KDR⁺ cells from the population of hematopoietic progenitor cells, thereby obtaining a purified population of long-term repopulating human hematopoietic stem cells. The invention also includes a cell obtained by this method.

The invention further includes the cell obtained by this method wherein the cell comprises an isolated nucleic acid.

In one aspect, the isolated nucleic acid is selected from the group consisting of a nucleic acid encoding adenosine deaminase, a nucleic acid encoding β-globin, a nucleic acid encoding multiple drug resistance, an antisense nucleic acid complementary to a human immunodeficiency virus nucleic acid, an antisense nucleic acid complementary to a nucleic acid encoding a cell cycle gene, and an antisense nucleic acid complementary to a nucleic acid encoding an oncogene.

In another aspect, the isolated nucleic acid is operably linked to a promoter/regulatory sequence.

In yet another aspect, the promoter/regulatory sequence is selected from the group consisting of a retroviral long terminal repeat, and the cytomegalovirus immediate early promoter.

The invention includes a method of expanding a population of long-term repopulating human hematopoietic stem cells. The method comprises obtaining a population of cells from human hematopoietic tissue, isolating a population of KDR+ hematopoietic stem cells therefrom, and incubating the population of KDR+ cells with vascula endothelial growth factor, thereby expanding the population of long-term repoputating human hematopoietic stem cells.

In one aspect, the method further comprises incubating the population of KDR+ cells with at least one growth factor.

In another aspect, the growth factor is selected from the group consisting of flt3 receptor ligand, kit receptor ligand, thrombopoietin, basic fibroblast growth factor, interleukin 6, interleukin 11, interleukin 3, granulomonocytic colony-stimulatory factor, granulocytic colony-stimulatory factor, monocytic colony-stimulatory factor, erythropoietin, angiopoietin, and hepatocyte growth factor.

The invention also includes an isolated purified population of long-term repopulating human hematopoietic stem cells obtained by this method.

The invention further includes a cell obtained using this method.

In one aspect, the cell comprises an isolated nucleic acid.

In another aspect, the isolated nucleic acid is selected from the group consisting of a nucleic acid encoding adenosine deamninase, a nucleic acid encoding β-globin, a nucleic acid encoding multiple drug resistance, an antisense nucleic acid complementary to a human immunodeficiency virus nucleic acid, an antisense nucleic acid complementary to a nucleic acid encoding a cell cycle gene, and an antisense nucleic acid complementary to a nucleic acid encoding an oncogene.

In yet another aspect, the isolated nucleic acid is operably linked to a promoter/regulatory sequence.

In a further aspect, the promoter/regulatory sequence is selected from the group consisting of a retroviral long terminal repeat, and the cytomegalovirus immediate early promoter.

The invention includes a blood substitute comprising the progeny cells of an isolated purified population of long term repopulating human hematopoietic stem cells.

In one aspect, the progeny cells are selected from the group consisting of red blood cells, neutrophilic granulocytes, eosinophilic granulocytes, basophilic granulocytes, monocytes, dendritic cells, platelets, B lymphocytes, T lymphocytes, natural killer cells, and differentiated precursors thereof, and undifferentiated progenitors thereof.

The invention also includes a chimeric non-human mammal comprising at least one of an isolated and purified long-term repopulating human hematopoietic stem cell.

In one aspect, the cell is introduced into the mammal using a method selected from the group consisting of transplantation, and blastocyst injection.

In another aspect, the mammal is selected from the group consisting of a mouse, a rat, a dog, a donkey, a sheep, a pig, a horse, a cow, a non-human primate.

The invention includes a method of inhibiting rejection of a transplanted organ. The method comprises ablating the bone marrow of a transplant recipient and administering to the recipient a multi-lineage engrafting dose of an isolated and purified long-term repopulating human hematopoietic stem cell obtained from the hematopoietic tissue of the donor of said organ, thereby inhibiting rejection of a transplanted organ.

The invention includes a method of transplanting an autologous human hematopoietic stem cell in a human. The method comprises obtaining a population of cells from the hematopoietic tissue of a human and isolating a population of non-malignant hematopoietic stem cells therefrom, ablating the bone marrow of the human, and administering at least one isolated non-malignant hematopoietic stem cell to the human, thereby transplanting an autologous human hematopoietic stem cell in a human.

The invention also includes a method of isolating a KDR+ cell. The method comprises selecting a cell expressing an antigen coexpressed with KDR, thereby isolating a KDR+ cell.

In one aspect, the coexpressed antigen is selected from the group consisting of a vascular endothelial growth factor receptor I, and a vascular endothelial growth factor receptor III.

The invention includes a method of isolating a KDR+ stem cell giving rise to at least one of a muscle cell, a hepatic oval cell, a bone cell, a cartilage cell, a fat cell, a tendon cell, and a marrow stroma cell. The method comprises isolating a KDR+ stem cell from hematopoietic tissue, thereby isolating a KDR+ stem cell giving rise to at least one of a muscle cell, a hepatic oval cell, a bone cell, a cartilage cell, a fat cell, a tendon cell, and a marrow stroma cell.

The invention includes a method of monitoring the presence of KDR+ stem cells in a human hematopoietic tissue in a human receiving therapy. The method comprises obtaining a sample of hematopoietic tissue from the human before, during and after the therapy, and measuring the number of KDR+ stem cells in the sample, thereby monitoring the presence of KDR+ stem cells in a human hematopoietic tissue obtained from a human receiving therapy.

DETAILED DESCRIPTION OF THE INVENTION

Figure 1A:
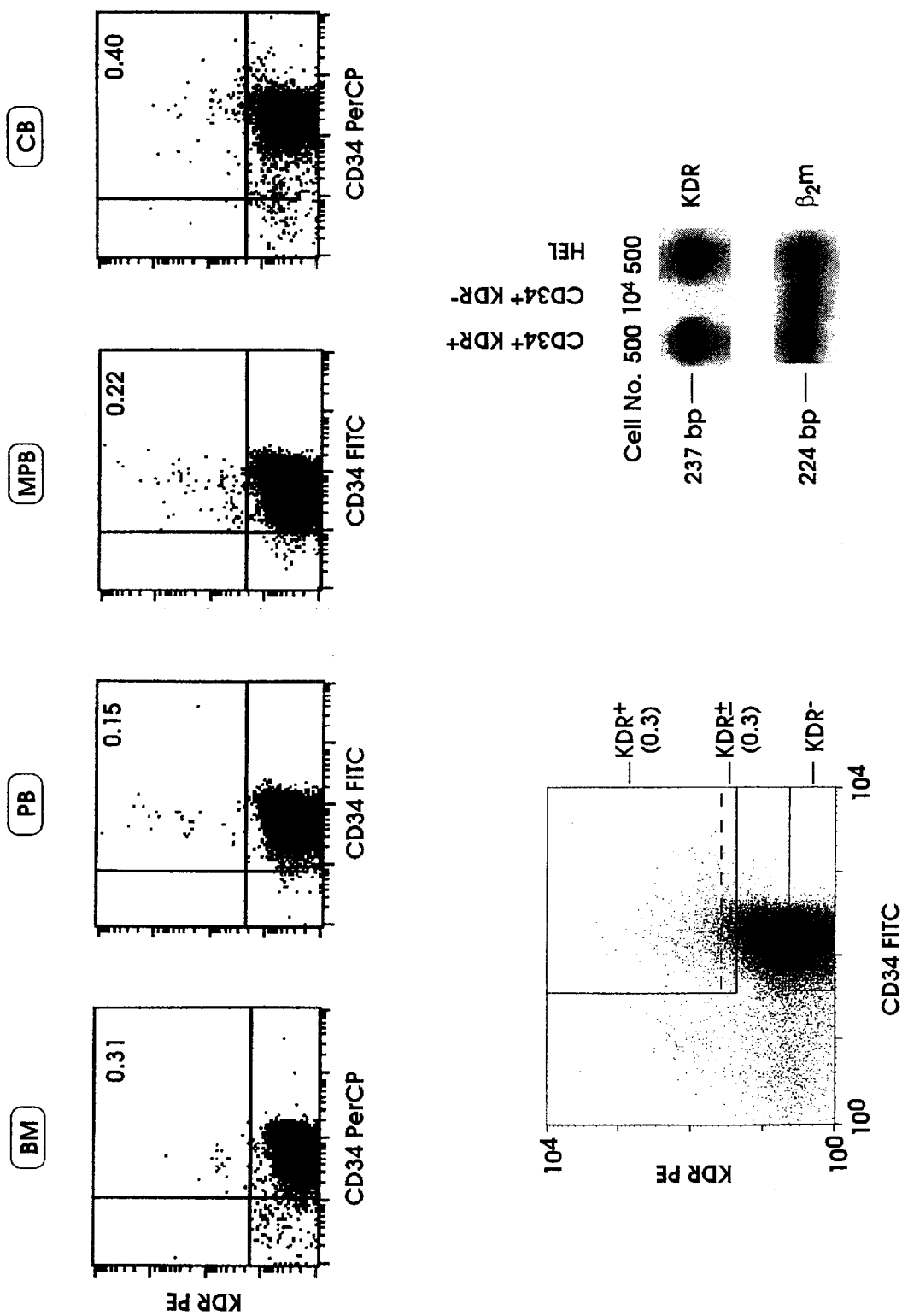
FIG. 1A is a graph depicting representative results on KDR expression and distribution of CD34+ cells by flow cytometry. KDR expression (top panels) detected by flow cytometry on bone marrow (BM), normal or mobilized peripheral blood (PB, MPB),and cord blood (CB) in CD34+ cells. Cells gated on physical parameters were analyzed for specific and nonspecific (isotype-matched) antibody reactivity (greater than about 40,000 cells were analyzed). The percentage of CD34+KDR+ cells is indicated by numbers on the figure. Bottom left: This graph depicts representative gates for analysis and sorting of KDR+ (KDR$^{bright}$), KDR+/±(KDR$^{dim}$) and KDR− CD34+ cells. A cord blood (CB) experiment is shown. The bottom right panel is an image of a gel depicting the RT-PCR analysis detecting the presence of KDR mRNA in CD34+KDR+ versus CD34+KDR− CB sorted cell populations.

The invention is based on the discovery that VEGFRII (KDR) is a key functional marker for long-term repopulating human HSCs. The identification of HSCs expressing KDR (i.e., KDR+ HSCs) serves to facilitate the development of improved methodology for the purification and characterization of long-term repopulating HSCs. The identification of KDR+ HSCs also serves to facilitate ex vivo expansion of purified HSCs by incubation of cells from hematopoietic tissue with VEGF combined with other hematopoietic growth factors (HGFs). Generation of chimeric animals (at the somatic level) through human HSC injection into the animal blastocyst generates human hematopoietic cells in this animal in vivo.

At a clinical level, purified KDR+ HSCs serve as key innovative tools for allogeneic or autologous HSC transplantation, as applied in leukemia/lymphoma, solid tumors, hematopoietic diseases and autoimmune disorders, and for HSC-based gene therapy for treatrment of a large spectrum of hereditary of acquired disorders affecting hematopoiesis and/or lymphopoiesis (e.g., AIDS). In addition, following in vitro expansion and differentiation of purified KDR+ HSCs, the KDR+ HSC progeny, for example, red blood cells, granulocytes and/or platelets, are useful in transfusion medicine.

The invention thus includes a method of obtaining a cell population enriched for long-term repopulating human hematopoietic stem cells. The method comprises obtaining a population of cells from human hematopoietic tissue. From the cells obtained from the hematopoietic tissue, cells expressing KDR on the surface of the cells are then isolated. In one embodiment, the KDR expressing cells are isolated using monoclonal antibody 260.4. However, the present invention should not be construed to be limited to isolation of KDR+ cells using any particular antibody. Rather, the present invention encompasses using any antibody which specifically binds KDR to isolate KDR+ cells including polyclonal antibody.

The invention also includes a method of obtaining a cell opulation enriched for long-term repopulating human hematopoieiic stem cells wherein KDR+ cells are isolated using a conjugated vascular endotbelial growth factor. This method simply capitalizes on the affinity of the KDR-VEGF receptor-ligand interaction to select cells expressing KDR on their surfaces by binding such cells, via the KDR present on the surface of the cell, to VEGF conjugated to, for example, a solid support matrix. Thus, the VEGF-conjugate can be used to afinity-puify the KDR expressing cells by standard methods well-known in the art.

The invention includes a population of cells obtained using this method.

One skilled in the art would appreciate, based upon the disclosure provided herlin, that the KDR+ cell fraction will not be comprised solely of long-term repopulating HSCs; instead, the fraction may include other cells such as megakaryocytes, endothelial cells, and the like, which express KDR but which are not HSCs. Preferably, these cells may be removed from the KDR+ HSCs by various methods well-known in the art based on the physical, biochemical, immunological, and/or morphological differences between these cells and the KDR+ undifferentiated hematopoietic progenitors and stem cells of interest. However, for purposes of the present invention, the non-HSC but KDR+ cells need not be removed from the KDR+ fraction isolated from human hematopoietic tissue.

Human hematopoietic tissue includes, but is not limited to, embryonic, fetal, and post-natal hematopoietic tissue. The embryonic hematopoietic tissue includes, for example, yolk sac and embryonic liver. Fetal hematopoietic tissue includes, but is not limited to, fetal liver, fetal bone marrow, and fetal peripheral blood. The post-natal hematopoietic tissue, in turn, includes cord blood, bone marrow, hepatic hematopoietic tissue, splenic hematopoietic tissue, and peripheral blood, both normal and mobilized.

The invention also includes a method of obtaining an enriched population of long-term repopulating HSCs that is starvation resistant. Starvation resistant cells are obtained by growing the KDR+ cells in mini-bulk culture under starvation conditions as described elsewhere herein. Starvation resistant cells obtained following culture constitute much fewer cell than are originally placed in serumn-free culture in the absence of any HGF treatment, except for VEGF addition. However, the resulting starvation-resistant cells comprise a much higher percentage of putative HSCs than an otherwise identical population of cells that are not grown under identical conditions, therefore, putative HSCs are further enriched in the KDR+ fraction as a result of the starvation selection. The particular conditions for starvation culture are set forth elsewhere herein. One skilled in the art, based upon the disclosure provided herein, would appreciate that the particular conditions, e.g., the precise number of days, may be varied so long as serum and HGFs are not added into the medium in any significant amount. The resultant starvation resistant cells, which are enriched for in vitro long-term repopulating HSCs, may then be used in a wide variety of applications as described elsewhere herein.

The invention includes a cell obtained by the above-disclosed method of obtaining a cell population enriched for long-term repopulating human hematopoietic stem cells.

Further, the invention includes a cell obtained using this method wherein the cell comprises an isolated nucleic acid. The nucleic acid may be introduced into the cell using any method for introducing a nucleic acid into a cell and such methods are well-known in the art and are described, for example, in Sambrook et al. (1989, In: Molecular Cloning: A Laboratory Manual, Cold Spring Harbor Laboratory Press, New York), and Ausubel et al. (1997, In: Current Protocols in Molecular Biology, Green & Wiley, New York). These methods include, but are not limited to, calcium phosphate precipitation transfection, DEAE dextran transfection, electroporation, microinjection, liposome-mediated transfer, chemical-mediated transfer, ligand-mediated transfer, and recombinant viral vector transfer, and the like.

The nucleic acid which may be transfected and/or transduced into the cell includes a nucleic acid such as that encoding adenosine deaminase, β-globin, and multidrug resistance. Thus, the cell may, if the nucleic acid is expressed, be used to provide the protein encoded thereby to the cell and/or to the extracellular milieu. The present invention should not be construed to be limited to these particular nucleic acids. Instead, a wide variety of nucleic acids encoding a plethora of proteins may be transfected into the cell of the invention. Thus, the invention should be construed to include nucleic acid products which are useful for the treatment of various disease states in a mammal. Such nucleic acids and associated disease states include, but are not limited to: DNA encoding glucose-6-phosphatase, associated with glycogen storage deficiency type 1A; DNA encoding phosphoenolpyruvate-carboxykinase, associated with Pepck deficiency; DNA encoding galactose-1 phosphate uridyl transferase, associated with galactosemia; DNA encoding phenylalanine hydroxylase, associated with phenylketonuria; DNA encoding branched chain α-ketoacid dehydrogenase, associated with Maple syrup urine disease; DNA encoding fumarylacetoacetate hydrolase, associated with tyrosinemia type 1; DNA encoding methylmalonyl-CoA mutase, associated with methylmalonic acidemia; DNA encoding medium chain acyl CoA dehydrogenase, associated with medium chain acetyl CoA deficiency; DNA encoding omithine transcarbamylase, associated with omithine transcarbamylase deficiency; DNA encoding argininosuccinic acid synthetase, associated with citrullinemia; DNA encoding low density lipoprotein receptor protein, associated with familial hypercholesterolemia; DNA encoding UDP-glucouronosyltransferase, associated with Crigler-Najjar disease; DNA encoding adenosine deaminase, associated with severe combined immunodeficiency disease; DNA encoding hypoxanthine guanine phosphoribosyl transferase, associated with Gout and Lesch-Nyan syndrome; DNA encoding biotinidase, associated with biotinidase deficiency; DNA encoding β-glucocerebrosidase, associated with Gaucher disease; DNA encoding β-glucuronidase, associated with Sly syndrome; DNA encoding peroxisome membrane protein 70 kDa, associated with Zellweger syndrome; DNA encoding porphobilinogen deaminase, associated with acute intermittent porphyria; DNA encoding a antitrypsin for treatment of α-1 antitrypsin deficiency (emphysema); DNA encoding erythropoietin for treatment of anemia due to thalassemia or to renal failure; and, DNA encoding insulin for treatment of diabetes. Such DNAs and their associated diseases are reviewed in Kay et al. (1994, T.I.G. 10:253–257) and in Parker and Ponder (1996, "Gene Therapy for Blood Protein Deficiencies," In: Gene Transfer in Cardiovascular Biology: Experimental Approaches and Therapeutic Implications, Keith and March, eds.).

One skilled in the art would appreciate, based upon the disclosure provided herein, that a human long-term repopulating hematopoietic stem cell able to engraft a recipient which cell comprises a nucleic acid is useful for gene therapy. That is, such a stem cell would, when introduced into an animal, express the nucleic acid thereby providing a method of producing a protein thus correcting a genetic defect in a cell, encode a protein which is not otherwise present in sufficient and/or functional quantity such that it corrects a genetic defect in the cell, and/or encodes a protein which is useful as a therapeutic in the treatment or prevention of a particular disease condition or disorder or symptoms associated therewith. Thus, long-term repopulating human hematopoietic stem cells are useful therapeutics allowing the expression of an isolated nucleic acid present in such cell.

The invention also includes a cell transfected with an antisense nucleic acid complementary to a nucleic acid encoding a retrovirus such as human immunodeficiency virus, a cell cycle gene, and an oncogene. One skilled in the art would appreciate, based upon the disclosure provided herein, that under certain circumstances, it is useful to inhibit expression of a nucleic acid. In this regard, certain molecules, including antisense nucleic acids and ribozymes, are useful in inhibiting expression of a nucleic acid complementary thereto.

Antisense molecules and their use for inhibiting gene expression are well known in the art (see, e.g., Cohen, 1989, In: Oligodeoxyribonucleotides, Antisense Inhibitors of Gene Expression, CRC Press). Antisense nucleic acids are DNA or RNA molecules that are complementary, as that term is defined elsewhere herein, to at least a portion of a specific mRNA molecule (Weintraub, 1990, Scientific American 262:40). In the cell, antisense nucleic acids hybridize to the corresponding MRNA, forming a double-stranded molecule thereby inhibiting the translation of genes.

The use of antisense methods to inhibit the translation of genes is known in the art, and is described, for example, in Marcus-Sakura, 1988, Anal. Biochem. 172:289. Such antisense molecules may be provided to the cell via genetic expression using DNA encoding the antisense molecule as taught by Inoue, 1993, U.S. Pat. No. 5,190,931 (incorporated by reference herein in its entirety).

Alternatively, antisense molecules of the invention may be made synthetically and then provided to the cell. Antisense oligomers of about 15 nucleotides are preferred, since they are easily synthesized and introduced into a target cell. Synthetic antisense molecules contemplated by the invention include oligonucleotide derivatives known in the art which have improved biological activity compared to unmodified oligonucleotides (see Cohen, supra; Tullis, 1991, U.S. Pat. No. 5,023,243, incorporated by reference herein in its entirety).

Ribozymes are another nucleic acid that may be transfected into the cell to inhibit nucleic acid expression in the cell. Ribozymes and their use for inhibiting gene expression are also well known in the art (see, e.g., Cech et al., 1992, J. Biol. Chem. 267:17479–17482; Hampel et al., 1989, Biochemistry 28:4929–4933; Eckstein et al., International Publication No. WO 92/07065; Altman et al., U.S. Pat. No. 5,168,053, incorporated by reference herein in its entirety). Ribozymes are RNA molecules possessing the ability to specifically cleave other single-stranded RNA in a manner analogous to DNA restriction endonucleases. Through the modification of nucleotide sequences encoding these RNAs, molecules can be engineered to recognize specific nucleotide sequences in an RNA molecule and cleave it (Cech, 1988, J. Amer. Med. Assn. 260:3030). A major advantage of this approach is that, because they are sequence-specific, only mRNAs with particular sequences are inactivated.

There are two basic types of ribozymes, namely, tetrahymena-type (Hasselhoff, 1988, Nature 334:585) and hammerhead-type. Tetrahymena-type ribozymes recognize sequences which are four bases in length, while hammerhead-type ribozymes recognize base sequences 11–18 bases in length. The longer the sequence, the greater the likelihood that the sequence will occur exclusively in the target mRNA species. Consequently, hammerhead-type ribozymes are preferable to tetrahymena-type ribozymes for inactivating specific mRNA species, and 18-base recognition sequences are preferable to shorter recognition sequences which may occur randomly within various unrelated mRNA molecules.

Ribozymes useful for inhibiting the expression of the proteins of interest may be designed by incorporating target sequences into the basic ribozyme structure which are complementary to the mRNA sequence of the nucleic acid encoding the protein of interest. Ribozymes targeting an immunodeficiency virus nucleic acid, a cell cycle gene, and an oncogene may be synthesized using commercially available reagents (Applied Biosystems, Inc., Foster City, Calif.) or they may be expressed from DNA encoding them.

The invention includes a cell comprising an isolated nucleic acid wherein the nucleic acid is operably linked to a promoter/regulatory sequence. Accordingly, expression of the nucleic acid in cells which do not normally express the nucleic acid may be accomplished by transfecting the cell with a nucleic acid operably linked to a promoter/regulatory sequence which serves to drive expression of the nucleic acid. Many promoter/regulatory sequences useful for driving constitutive expression of a gene are available in the art and include, but are not limited to, for example, the cytomegalovirus immediate early promoter enhancer sequence, the SV40 early promoter, the Rous sarcoma virus promoter, and the like. Inducible and tissue specific expression of the nucleic acid operably linked thereto may be accomplished by placing the nucleic acid under the control of an inducible or tissue specific promoter/regulatory sequence. Examples of tissue specific or inducible promoter/regulatory sequences which are useful for this purpose include, but are not limited to the MMTV long terminal repeat (LTR) inducible promoter, and the SV40 late enhancer/promoter. In addition, promoters which are well known in the art which are induced in response to inducing agents such as metals, glucocorticoids, and the like, are also contemplated in the invention. Thus, it will be appreciated that the invention should be construed to include the use of any promoter/regulator sequence which is either know or is heretofore unknown, which is capable of driving expression of the nucleic acid operably linked thereto.

The invention also includes a method of obtaining a purified population of human HSCs. The method comprises two steps. The first step involves the purification of hematopoietic progenitor cells from cells obtained from human hematopoietic tissue. Such progenitor cells, or blasts, may be purified by various methods capitalizing on the difference(s) in a physical property (e.g., the cell density), a biochemicalibiological property (e.g., the ability to take up a dye), and/or the expression of various surface markers, using established procedures well-known in the art.

In one embodiment, CD34$^+$ HPCs were isolated using established procedures described herein, wherein the CD34$^+$ HPCs are obtained from embryonic fetal liver (FL), cord blood (CB), adult bone marrow (BM) and normal or mobilized peripheral blood (PB, MPB). The preferred method for purification of these cells is by use of the miniMACS Multisort CD34 isolation system (Miltenyi, Bergisch Gladbach, Germany). However, other methods known in the art for purification of hematopoietic progenitor cells, including CD34$^+$ cells, or methods to be developed, may also be used to practice the present invention.

Further, although CD34 marker was used to isolate HPCs, other early markers such as c-kit, CD38, Thy-1, and AC133, and the like, may also be used to isolate such cells.

In addition, CD34$^-$ cells which are also lin$^-$ may also be used as the population of HPCs which are then processed according to the second step of the method. As disclosed herein in the examples below, CD34$^-$lin$^-$KDR$^+$ cells also comprise HSCs and these cells are able to engraft non-human animals just as CD34$^+$KDR$^+$ cells also engraft theseanimals. Thus, the CD34$^-$lin$^-$ cells also comprise a useful population enriched for undifferentiated cells from which long-term repopulating human hematopoietic cells may be isolated.

CD34$^+$ versus CD34$^-$ cells and lin+ versus lin− cells may be separated from each other by, for example, fluorescence activated cell sorting as disclosed herein. However, the present invention should not be construed to be limited to this method of selecting cells on the basis of the expression of various cell surface markers. Rather, other methods well-known in the art for obtaining fractions of cell populations are also encompassed by the present invention.

In the second step, the human hematopoietic progenitor cells isolated previously are selected for the expression of KDR. In one embodiment, the HPCs were separated by cell sorting into CD34$^+$KDR$^+$ (KDR$^{bright}$), CD34$^+$KDR$^{+/\pm}$ (KDR$^{dim}$) and CD34$^+$KDR$^{31}$ cells using anti-KDR monoclonal antibody (i. e., the 260.4 clone available from Gesellschaft fir Biologische Forchung, GBF, Braunschweig, Germany, or any other MoAb or molecule recognizing KDR$^+$ cells).

Other methods known in the art for separation of cell subsets or methods to be developed, may also be used to practice the present invention. The herein described purification of KDR$^+$ cells may be modified by using any other reagent or combination of reagents such as any MoAb or combination of MoAbs used together with any reagent (e.g., MoAbs) which specifically bind KDR. Thus, the present invention should not be construed to be limited to using MoAb 260.4, or any other antibody, to isolate cells expressing KDR.

Further, as discussed previously elsewhere herein, other early markers besides CD34 may be used to select human long-term repopulating HSCs in conjunction with KDR. As an example, AC133 is expressed on immature hematopoietic progenitor cells and stem cells (Miraglia et al., 1997, Blood 90:5013–5021; Yin et al., 1997, Blood 90:5002–5012). AC133 MoAbs recognize 20–60% of CD34$^+$ cells including CD34$^{+bright}$, CD38$^{-/dim}$, HLA-DR$^-$, CD90$^+$ and CD117$^+$ cells. Thus, instead of using CD34$^+$ or CD34$^-$ cells expressing KDR AC133$^+$ or AC133$^-$ cells expressing KDR may be utilized. The invention described herein, therefore, includes all reagents when used together with any reagent recognizing KDR such as, but not limited to, other early markers including c-kit receptor, Thy-1, vascular endothelial growth factor receptor I, vascular endothelial growth factor receptor III, Tie1, Tek, basic fibroblast growth factor receptor, flt3 receptor, and AC133, as well as the selection of cells which are negative for late markers such as lin, and the like.

Receptor-type tyrosine kinases (RTKs) constitute a family of proteins involved in growth and developmental processes activating various cellular responses during embryogenesis and adult life. To further characterize CD34$^+$ that express KDR RT-PCR for detection of RTKs VEGFRI (flt1), VEGFRIII (flt4), Tie1 and Tek in these KDR$^+$ subsets was applied by using RT-PCR methodology previously described in detail (Ziegler et al., 1999, Blood 93:3355–3368). RT-PCR analysis provided evidence that RTKs Flt1, Flt4, Tie1 and Tek were expressed at transcriptional level in small numbers of highly purified CD34$^+$KDR$^+$. Thus, CD34$^+$ cells expressing KDR may be further subdivided into subsets that express or not RTKs by using RTK specific antibodies or any other reagent recognizing RTKs. The invention thus includes all technologies/methodologies aimed to further subdivide the CD34$^+$ population that are KDR$^+$ by means of reagents recognizing the above mentioned RTKs, any other RTKs or any other cell surface structure expressed on KDR$^+$ populations.

Thus, the invention includes a method of isolating a KDR+ cell by selecting for cells expressing an antigen coexpressed with KDR on the surface of cells. Such antigens coexpressed with KDR include, for example, VEGFRI (flt1), VEGFRIII (flt4). Thus, KDR+ cells may be isolated by selecting for cells that express VEGFRI and/or VEGFRIII which are known to coexpress with KDR.

The purified human HSCs in the KDR$^+$ and KDR$^{31}$ cell population are then assayed based upon their capacity for long term hematopoietic repopulation in vitro and in vivo. In parallel, the HPCs present in these two cell populations are assayed for their capacity for in vitro short term generation of a hematopoietic progeny. The long-term repopulation HSCs, defined according to the criteria described in the Examples section, are virtually exclusively contained within the CD34$^+$KDR$^+$ and CD34$^+$KDR$^{+/\pm}$ fractions. Conversely, unilineage and bilineage HPCs are almost exclusively contained within the CD34$^+$KDR$^-$ fraction. This method of purification of HSCs from CB, adult BM and PB or MPB yields a suitable number of HSCs for in vitro and in vivo clinical use. The most preferred sources of purified HSCs are post-natal hematopoietic tissues (e.g., CB, adult BM, PB, and MPB). However, other hematopoietic tissue sources include, for example, embryonic hematopoietic tissue (e.g., yolk sac and embryonic liver), fetal hematopoietic tissue (e.g., fetal liver, fetal bone marrow, and fetal peripheral blood).

The invention further includes a population of cells and a cell obtained using the above-disclosed method.

The invention also includes further purifying the population of long-term repopulating HSCs by growing CD34$^+$KDR$^+$ or CD34$^+$KDR$^{+/\pm}$ cells in mini-bulk culture under starvation conditions as described elsewhere herein. Starvation resistant cells obtained following culture constitute approximately 10–25% of the initial number of cells placed in serum-free culture in the absence of any HGF treatment, except for VEGF addition. However, the resulting starvation-resistant cells comprise approximately ≧80–95% putative HSCs thereby being greatly enriched as a result of the starvation selection. The particular conditions for starvation culture are set forth elsewhere herein. One skilled in the art, based upon the disclosure provided herein, would appreciate that the particular conditions, e.g., the precise number of days, may be varied so long as serum and HGFs are not added into the medium in any significant amount. The resultant starvation resistant cells, which are greatly enriched for in vitro long-term repopulating HSCs, may then be used in a wide variety of applications as described elsewhere herein. The invention includes a population of cells and a cell isolated by this method.

In addition, the invention includes a cell obtained by the above-disclosed method which cell comprises a nucleic acid. As described previously elsewhere herein, the nucleic acid may be operably linked to a promoter/regulatory sequence and/or may encode a variety of proteins and/or nucleic acids which are expressed by the cell and/or which inhibit expression of a nucleic acid complementary to the nucleic acid introduced into the cell.

The invention also includes a method of expanding human HSCs in vitro for use in either ex vivo or in vivo therapy. The method comprises obtaining a population of $KDR^+$ stem cells according to the above described method and incubating this cell population in the presence of VEGF. Further, the invention includes a population of cells and a cell obtained using this method.

In addition, the invention includes incubating KDR+ cells in the presence of VEGF and at least one other growth factor. As the data presented herein establish, treatment of the $CD34^+KDR^+$ cell population with VEGF results in a significant increase in the number of HSCs. Addition of both VEGF and other suitable HGFs, as indicated herein, results in a marked amplification of the generated primitive HPCs, i.e., approximately a 150-fold amplification of $CD34^+/CD38^+$ HPCs. In one aspect, the HGFs include, but are not limited to, flt3 receptor ligand, kit receptor ligand, thrombopoietin, basic fibroblast growth factor, interleukin 6, interleukin 3, interleukin 11, granulomonocytic colony-stimulatory factor, granulocytic colony-stimulatory factor, monocytic colony-stimulatory factor, erythropoietin, angiopoietin, and hepatocyte growth factor.

Purified HPCs may be differentiated for use in transfusion medicine. In this regard, a combined step procedure is applied to cells in culture. In one step, the purified $CD34^+KDR^+$ and/or the $CD34^-lin^-KDR^+$ population of long-term repopulating human HSCs is amplified which results in the generation of HSCs/HPCs by addition of VEGF and other suitable HGFs as described herein. In another step, the generated HSC/HPC population is grown in culture conditions which selectively channel the HPCs into differentiation and maturation through the erythroid or megakaryocytopoietic or granulopoietic/neutrophilic or monocytopoietic pathway (Labbaye et al., 1995, J. Clin. Invest. 95:2346–2358; Guerriero et al., 1995, Blood 86:3725–3736; Gabbianelli et al., 1995, Blood 86:1661–1670) or other hematopoietic pathways including granulopoietic/eosinophilic or basophilic, or dendritic cells, or B, or T lymphopoietic or NK cell pathways. Other methods known in the art for hematopoietic cell production or methods to be developed, may also be used.

Purified HSCs are also useful in a variety of clinical settings. For example, HSCs may be used as delivery vehicles for the administration of nucleic acid which is a therapeutic product or a nucleic acid encoding a therapeutic product (i.e., an RNA or protein molecule) to a human. For example, HSCs are transfected/transduced with a suitable nucleic acid, preferably operably linked to a suitable promoter/regulatory sequence, wherein when the nucleic acid is expressed in the HSCs, a therapeutic RNA or protein is produced which is of benefit to the human. Delivery of a nucleic acid to HSCs is accomplished using standard technology, for example, using viral gene transfer, described, for example, in Verma et al. (1997, Nature 389:239–242).

HSCs comprising an isolated nucleic acid may be readily introduced into the circulating blood by intravenous injection or infusion, intraperitoneal injection or infusion and even by intrauterine injection of infusion. Following delivery of HSCs to the circulating blood, they home to bone marrow microenvironmental niches.

Therapeutic nucleic acids which are suitable for introduction into HSCs include, but are not limited to, nucleic acid encoding adenosine deaminase or a biologically active fragment thereof, for treatment of severe combined immunodeficiency, the gene encoding $\beta$-globin, or a biologically active fragment thereof, for treatment of $\beta$-thalassemia or sickle cell anemia, a nucleic acid comprising an antisense HIV sequence, for example, an anti-tat nucleic acid sequence, for treatment of HIV infection, a nucleic acid encoding a multidrug resistance gene to facilitate drug resistance in transfected cells during treatment of neoplasia, and the like.

Suitable promoter/regulatory sequences include, but are not limited to, the retroviral LTR and the cytomegalovirus immediate early promoter.

The invention also includes a blood substitute comprising the progeny cells derived from an isolated purified population of long-term repopulating human hematopoietic stem cells as described in the experimental examples that follow.

In one aspect, the blood substitute comprises multi-oligo- and/or unipotent progenitors. In another aspect the blood substitute comprises red blood cells and/or neutrophilic granulocytes and/or eosinophilic granulocytes and/or basophilic granulocytes and/or monocytes and/or platelets, among other cells and/or components of normal blood. In another aspect the blood substitute comprises dendritic cells and/or T and/or B lymphocytes and/or NK cells. The physiological functions of the blood substitute described herein comprise the long-term repopulating HSC which permanently and completely reconstitutes the hematopoietic system of a myeloablated host, differentiated/ differentiating progeny generated from the cell(s) described previously elsewhere herein by ex vivo manipulation procedures yielding multi-, oligo- and/or unipotent progenitors or terminal differentiated cells of the erythroid, granulocytic, monocytic, dendritic/antigen-presenting cells, megakaryocytic, T- and B-lymphoid, and natural killer (NK) cell series. These blood elements function as oxygen carriers (erythroid elements), phagocytes protecting the organism against infection (neutrophilic, eosinophilic, basophilic, granulocytes and monocytes/macrophages), producers (plasma cells/B-lymphocytes) of immunoglobulins (humoral immunity) which react with particular antigens, antigen-recognizing cells (T-cells; cell-mediated immunity), antigen-presenting cells (such as dendritic cells which process antigens intracellularly to peptides and present them together with MHC Class I or II molecules to CD8 and CD4 T-lymphocytes, respectively), cells killing other cells directly or by antibody-dependent cell-mediated cytotoxicity (ADCC) which they recognize as foreign (NK cells, lymphokine-activated killer cells, i.e., LAK cells), producers of platelets (megakaryocytes) which play a central role in the haemostatic response to vascular injury.

The invention also includes a method of obtaining a purified population of long-term repopulating human hematopoietic stem cells that are $CD34^-lin^-KDR^+$, as these are defined by the examples set forth below. The method comprises obtaining a population of CD34⁻lin³¹ (lineage marker negative) cells and isolating a KDR⁺ population therefrom. This is because, as more fully set forth below, CD34⁻lin⁻KDR⁺ cells comprise another population comprising long-term repopulating human HSCs. Indeed, without wishing to be bound by theory, the CD34⁻lin⁻KDR⁺ cells may convert to their CD34⁺ counterparts in vivo as CD34⁻lin⁻ cells convert into CD34⁺lin⁻ cells in vitro (Zanjani et al., 1998, Blood (Suppl. I) 92:504). Therefore, a purified population of long-term repopulating HSCs may be obtained by first selecting for CD34⁻lin⁻ by fluorescence activated cell sorting or by use of immunobeads as described elsewhere herein for isolation of CD34⁺ cells and then further selecting from the CD34⁻lin⁻ population the subfraction of KDR⁺ as described elsewhere herein. The use of antibodies specific for human cell markers to obtain purified populations of cells is well-known in the art and is described elsewhere herein. Other methods known in the art for separation of cell subsets or methods to be developed, may also be used to practice the present invention, as discussed above for CD34⁺ and CD34⁺KDR⁺ cell populations.

The long-term repopulating HSCs obtained by selecting for a population of CD34⁻lin⁻KDR⁺ cells may then be used similarly to the CD34⁺KDR⁺ previously described elsewhere herein such as, for example, as a blood substitute, for administration of a nucleic acid which is therapeutic, and/or in transplantation medicine.

The invention includes a chimeric mammal engrafted with at least one of an isolated purified long-term repopulating human hematopoietic stem cell. That is, the invention includes a mammal that has received an HSC from another mammal or an autologous transplant wherein the HSC is reintroduced into the mammal after being isolated and purified from that same mammal by ex vivo methods such as those described elsewhere herein. Thus, HSCs isolated from a mammal may be re-introduced into the same mammal or another mammal perhaps after a nucleic acid has been introduced into the cell. The present invention should be construed to encompass the introduction of a nucleic acid into a mammal by the process of introducing an isolated nucleic acid into an HSC removed from that animal and using the HSC to engraft the animal. The HSCs may be isolated from the same recipient animal or it may be obtained from another donor animal of the same or a different species. However, the invention should not be construed to be limited to only this method of producing a chimeric animal. Instead, the invention encompasses the production of a chimeric animal by other methods well known in the art such as, but not limited to, blastocyst injection. Such methods are well-known in the art.

The introduction of an isolated nucleic acid into an HSC has been described elsewhere herein and the methods for expanding the HSCs and for introducing them and thereby engrafting an animal with the cells are described elsewhere herein. One skilled in the art, based upon the disclosure provided herein, would be able to generate a chimeric mammal engrafted by at least one isolated repopulating HSC by intravenous transfusion into the animal. However, any other method of delivering repopulating HSCs to mammal recipients may be used. Further, the recipient animal's hematolymphopoietic system may be either ablated before engraftment of the cell or the cell(s) are introduced into the animal in addition to the animal's own hematopoietic system.

Hematopoietic multilineage engraftment in the recipient mammal is defined as permanent and complete, i.e., reconstitution of all hematopoietic lineages through donor HSCs, as well as sustained production of HPCs. Multilineage engraftment is detectable through specific MoAbs recognizing cells pertaining to a particular lineage. As an example, erythroid cells are recognized by anti-glycophorin A (GPA) MoAb, MKs are recognized by MoAbs such as anti-CD61 or -CD41, and HPCs are recognized by clonogenic assay and anti-CD34⁺, anti-AC133 MoAbs, and the like.

The invention also includes a method of inhibiting rejection of a transplanted organ. The method comprises engrafting the organ recipient using an isolated and purified long-term repopulating human hematopoietic stem cell obtained from the organ donor prior to transplanting the organ. The bone marrow of the recipient is ablated by standard methods well known in the art. Generally, bone marrow ablation is accomplished by X-radiating the animal to be transplanted, administering drugs such as cyclophosphamide or by a combination of X-radiation and drug administration. In some embodiments, bone marrow ablation is produced by administration of radioisotopes known to kill metastatic bone cells such as, for example, radioactive strontium, ¹³⁵Samarium, or ¹⁶⁶Holmium (Applebaum et al., 1992, Blood 80:1608–1613). By engrafting the hematopoietic system of the recipient with HSCs from the organ donor, rejection of the transplanted organ is thereby inhibited.

Similarly, the invention includes a method of transplanting an autologous human hematopoietic stem cell in a human. The method comprises isolating a population of long-term repopulating stem cells from the recipient and ablating the bone marrow of the recipient. Non-malignant long-term repopulating stem cells are then isolated by selecting for KDR⁺ cells as disclosed previously elsewhere herein. Non-malignant cells are identified within a population of KDR⁺ cells based on various criteria well-known in the art including, but not limited to, the cell morphology, biochemical properties, growth characteristics, and the expression of specific tumor cell markers. Thus, the bone marrow of the individual is purged of malignant blasts and other malignant cells such that by transplanting the non-malignant stem cells back into to the individual, diseases such as melanomas may be treated. That is, for diseases where the malignant cells do not express KDR, the bone marrow may be ablated and cells previously obtained from the individual may be enriched for non-malignant long-term repopulating hematopoietic stem cells and returned to the patient where they cause multilineage engraftment thereby treating or alleviating the disease.

The invention includes a method of isolating a KDR⁺ stem cell giving rise to at least one of a skeletal muscle cell and a hepatic oval cell. The method comprises isolating a population of long-term repopulating HSCs by selecting for KDR⁺ cells from cells obtained from human hematopoietic tissue as disclosed previously elsewhere herein. Recent data demonstrate stem cells associated with the bone marrow has epithelial cell lineage capability in that the cells gave rise to repopulating liver cells in transplanted rats (Petersen et al., 1999, Science 284:1168–1170). Similarly, Ferrari et al. (1998, Science 279:1528–1530), demonstrated that unfractionated bone marrow cells, when injected into recipient muscle, migrated to sites of muscle damage, and gave rise to marrow-derived cells which underwent myogenic differentiation and participated in regeneration of damaged muscle fibers. Further, bone marrow cells have the potential to differentiate to lineages of mesenchymal tissues, including bone, cartilage, fate, tendon, muscle and marrow stroma (Pittenger et al., 1999, Science 284:143–147). Thus, mesenchymal, hepatic and myogenic progenitors may be recruited from marrow-derived cells. Without wishing to be bound by theory, the stem cells which gave rise to hepatic oval cells and myogenic progenitors are likely to be the long-term repopulating KDR⁺ stem cells of the present invention. Thus, by isolating KDR+ stem cells as disclosed herein, it is possible to derive cells with epithelial cell and/or myogenic capability.

The invention includes a method of monitoring the presence of KDR⁺ stem cells in a human hematopoietic tissue in a human receiving therapy. The method comprises obtaining a hematopoietic tissue sample from the human and measuring the number of KDR+ stem cells in the sample. Measurements are made before, during and after therapy where therapy may be chemotherapy and/or radiation therapy which is known to affect the stem cell compartment such as, for example, myeloablation therapy or therapy known to cause hematopoietic suppression. Until the present invention, no method was available to allow the status of the stem cell compartment to be determined during such therapy. The present invention, by defining a marker, i.e., KDR⁺, for the cells of this compartment, allows the determination of the status of the stem cell compartment in a patient receiving therapy known or thought to affect the stem cell compartment at any point before, during, and after therapy.

DEFINITIONS

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

The term "antibody", as used herein, refers to an immunoglobulin molecule which is able to specifically bind to a specific epitope on an antigen.

Antibodies can be intact immunoglobulins derived from natural sources or from recombinant sources and can be immunoreactive portions of intact immunoglobulins.

Antibodies are typically tetramers of immunoglobulin molecules. The antibodies in the present invention may exist in a variety of forms including, for example, polyclonal antibodies and humanized antibodies (Harlow et al., 1999, In: Using Antibodies: A Laboratory Manual, Cold Spring Harbor, N.Y.; Harlow et al., 1988, In: Antibodies: A Laboratory Manual, Cold Spring Harbor, N.Y.; Houston et al., 1988, Proc. Natl. Acad. Sci. U.S.A. 85:5879–5883; Bird et al., 1988, Science 242:423–426). By the term "specifically binds", as used herein, is meant, for example, an antibody which recognizes and binds CD34 polypeptide, but does not substantially recognize or bind other molecules in a sample. Similarly, an antibody "specifically binds KDR" if the antibody recognizes and binds VEGFR2/KDR/flk-1 in a sample but does not substantially recognize or bind to other molecules in a sample. Further, an antibody specifically binds lin markers if the antibody recognizes and binds lineage markers but does not substantially recognize or bind to other molecules in a sample.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

As used herein, the term "antisense nucleic acid" means a nucleic acid polymer, at least a portion of which is complementary to another nucleic acid. The antisense nucleic acid may comprise between about fourteen and about fifty or more nucleotides. Preferably, the antisense nucleic acid comprises between about twelve and about thirty nucleotides. More preferably, the antisense nucleic acid comprises between about sixteen and about twenty-one nucleotides. The antisense nucleic acid may include, but is not limited to, phosphorothioate oligonucleotides and other modifications of oligonucleotides. Methods for synthesizing oligonucleotides, phosphorothioate oligonucleotides, and otherwise modified oligonucleotides are well known in the art (U.S. Pat. No: 5,034,506; Nielson et al., 1991, Science 254:1497).

The term "antisense" refers particularly to the nucleic acid sequence of the non-coding strand of a double stranded DNA molecule or, in the case of some viruses, a single or double stranded RNA molecule, encoding a protein, or to a sequence which is substantially homologous to the non-coding strand. It is not necessary that the antisense sequence be complementary solely to the coding portion of the coding strand of the nucleic acid molecule. The antisense sequence may be complementary to regulatory sequences specified on the coding strand of a nucleic acid molecule encoding a protein, which regulatory sequences control expression of the coding sequences.

The term "sense", as used herein, refers to the nucleic acid sequence of the single or double-stranded nucleic acid molecule which encodes a protein, or a sequence which is substantially homologous to that strand. However, the nucleic acid sequence is not limited solely to the portion of the coding strand encoding a protein; rather, the sequence may include regulatory sequences involves in, for example, the control of expression of the coding sequence.

The term "biochemical/biological property," as used herein, means any biochemical/biological property of a cell which allows the purification of such cell. A biochemical/biological property includes, for example, the ability of a cell to take up or exclude certain dyes.

"Blood substitute," as used herein, refers to a substance derived from long-term repopulating human hematopoietic stem cells comprising at least one component of naturally-occurring blood such as, for example, red blood cells, platelets, and other components/products of normal blood. Further, the blood substitute refers to a substance that can perform at least one of the biochemical/physiological functions of normal blood such as the transport of oxygen, and the like.

By "chimeric mammal" as the term is used herein, is meant any mammal which is a recipient of at least one long-term repopulating human HSC from another mammal.

"Complementary" as used herein refers to the broad concept of subunit sequence complementary between two nucleic acids, e.g., two DNA molecules. When a nucleotide position in both of the molecules is occupied by nucleotides normally capable of base pairing with each other, then the nucleic acids are considered to be complementary to each other at this position. Thus, two nucleic acids are complementary to each other when a substantial number (at least 50%) of corresponding positions in each of the molecules are occupied by nucleotides which normally base pair with each other (e.g., A:T and G:C nucleotide pairs).

By the terms "coding" and "encoding", as these terms are used herein, is meant that the nucleotide sequence of a nucleic acid is capable of specifying a particular polypeptide of interest. That is, the nucleic acid may be transcribed and/or translated to produce the polypeptide. Thus, for example, a nucleic acid encoding adenosine deamininase is capable of being transcribed and/or translated to produce an adenosine deamininase polypeptide. "Coexpressed," as the term is used herein, means that the antigen is expressed on or in a cell which also comprises detectable KDR antigen. However, the two molecules need not be coexpressed contemporaneously. Rather, it is sufficient that the cell express both KDR and the coexpressed antigen at some point in time such that selection of a cell expressing the other antigen selects for cells which either at that moment, or at some later time, also express KDR.

The term "early marker," as used herein, means any antigen on the surface of a cell which is preferentially or selectively expressed on the surface of undifferentiated precursor cells compared to its expression on the surface of differentiated cells. Examples of early markers for hematopoietic cells include, but are not limited to, CD34, Thy-1, c-kit receptor, flt3 receptor, AC 133, vascular endothelial growth factor receptor I, vascular endothelial growth factor receptor III, Tie1, Tek, and basic fibroblast growth factor receptor.

By "engrafted", as the term is used herein, is meant that the mammal comprises a hematolymphopoietic system repopulated by multi-lineage cells derived from at least one isolated purified HSC which was administered to the animal.

The term "enriched," as used herein, means that a population of cells comprises a detectably higher level of the enriched cell type than an otherwise identical cell population not subjected to selection for that cell type. The level of enrichment may be determined by comparing the number of cells of interest in an unselected population to the number of cells of interest in a population selected for a particular trait or marker by a cell selection method.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

The term "KDR$^+$," as used herein, means the cell expresses detectable KDR antigen. The antigen may be detected by a variety of methods including PCR, RT-PCR, Western blotting, and immunofluorescence. With regard to immunofluorescence, KDR$^+$ cells may be designated KDR$^+$ (i.e., KDR$^{bright}$) and KDR$^{+/\pm}$ (i.e., KDR$^{dim}$) when stained using the anti-KDR monoclonal antibody 260.4 under the conditions disclosed elsewhere herein.

By the term "late marker," as used herein, is meant a marker associated with or preferentially expressed on differentiated precursor cells. Such markers include, but are not limited to, the lineage (lin) markers.

By the term "multi-lineage engrafting dose", as the term is used herein, is meant at least one long-term repopulating human hematopoietic stem cell which, when transplanted into an animal, is capable of giving rise to detectable multi-lineage engraftment of the recipient animal.

"Non-malignant," as the term is used herein, means that a cell does not exhibit any detectable traits typically associated with neoplastic cells such as the loss of contact-inhibition, and the like.

The term "physical property," as used herein, means any property of a cell which may be used to physically isolate such cell. For example, physical properties of a cell include, but are not limited to, the cell size, density, mass, and morphology.

As used herein, the term "promoter/regulatory sequence" means a DNA sequence which is required for expression of a gene operably linked to the promoter/regulator sequence. In some instance, this sequence may be the core promoter sequence and in other instances, this sequence may also include an enhancer sequence and other regulatory elements which are required for expression of the gene in a tissue-specific manner.

By describing two nucleic acid sequences as "operably linked" as used herein is meant that a single-stranded or double-stranded nucleic acid moiety comprises each of the two nucleic acid sequences and that the two sequences are arranged within the nucleic acid moiety in such a manner that at least one of the two nucleic acid sequences is able to exert a physiological effect by which it is characterized upon the other.

By "starvation resistant," as the term is used herein, is meant that a cell has the ability to survive at least about 5–10 days (shorter starvation times may apply) in liquid suspension culture in FCS-free and serum-free medium (or any other type of suitable medium) in absence of added HGFs, except VEGF, under the conditions described elsewhere herein. "Transfected" or "Transduced", as the term is used herein, encompasses any method by which an isolated nucleic acid may be introduced into a cell. Such methods are well known in the art and are described in, for example, Sambrook et al. (1989, Molecular Cloning: A Laboratory Manual, Cold Spring Harbor Laboratory Press, New York) and Ausubel et al. (1997, Current Protocols in Molecular Biology, Green & Wiley, New York). For instance, the nucleic acid may be introduced into a cell using a plasmid or viral vector, electroporation, a "gene gun", polylysine compounds, and the like.

By the term "vector" as used herein, is meant any plasmid or virus encoding an exogenous nucleic acid. The term should also be construed to include non-plasmid and non-viral compounds which facilitate transfer of nucleic acid into virions or cells, such as, for example, polylysine compounds and the like. The vector may be a viral vector which is suitable as a delivery vehicle for delivery of the isolated nucleic acid of interest (e.g., adenosine deamininase, β-globin, multidrug resistance, and the like) to a cell, or the vector may be a non-viral vectors which is suitable for the same purpose. Examples of viral and non-viral vectors for delivery of nucleic acids to cells and tissues are well known in the art and are described, for example, in Ma et al. (1997, Proc. Natl. Acad. Sci. U.S.A. 94:12744–12746). Examples of viral vectors include, but are not limited to, a recombinant vaccinia virus, a recombinant adenovirus, a recombinant retrovirus, a recombinant adeno-associated virus, a recombinant avian pox virus, and the like (Cranage et al., 1986, EMBO J. 5:3057–3063; International Patent Application No. WO94/17810, published Aug. 18, 1994; International Patent Application No. WO94/23744, published Oct. 27, 1994). Examples of non-viral vectors include, but are not limited to, liposomes, polyamine derivatives of DNA, and the like.

The invention will be further described by reference to the following experimental examples. These examples are provided for purposes of illustration only, and are not intended to be limiting unless otherwise specified. Thus, the invention should in no way be construed as being limited to the following examples, but rather, should be construed to encompass any all variations which become evident as a result of the teaching provided herein.

EXAMPLES

The experiments which are presented herein examine the expression and functional role of VEMFR, particularly the VEGFRII termed flk1/KDR, in HPCs/HSCs purified from embryonic-fetal liver (FL), cord blood (CB), normal or mobilized adult peripheral blood (PB, MPB) and adult bone marrow (BM). As indicated herein, these purified lin (lineage marker negative) HPC populations comprise a small minority of HSCs. The data may be summarized as follows.

KDR expression on purified $CD34^+$ HPC populations was analyzed using a monoclonal antibody (MoAb) which recognizes the extracellular receptor domain.

MoAb evaluation indicated that KDR is expressed on approximately <1% CB, BM, PB or MPB $CD34^+$ cells under the conditions used herein. Representativeresults using this MoAb. indicated that KDR is expressed on approximately $\geq 1\%$ FL $CD34^+$ cells. Without wishing to be bound by theory, other antibodies and/or varying detection conditions may affect the percentage of KDR+ cells detected in a CD34+ population of cells.

KDR expression is virtually restricted to adult and CB HSCs and a portion of the most primitive subset of adult and CB HPCs. KDR is also expressed on approximately =1% of $CD34^-lin^-$ cells.

The $KDR^+$ versus $KDR$ cell fractions were sorted from $CD34^+$ HPCs purified from CB, BM, PB or MPB. In both cell fractions, the following assays were performed: (i) Assay of HPCs in clonogenic culture; (ii) assay of long-term repopulating HSCs in vitro (i.e., evaluation in 12 week LTC of the frequency of CAFCs and/or LTC-ICs: the frequency was evaluated by limiting dilution assay (LDA)) and in vivo, i.e., analysis of hematopoietic repopulation in NOD-SCID mice at 3 months after sublethal irradiation and cell injection. The results consistently established that the $CD34^+$ $KDR^+$ and/or the $CD34^+KDR^{+/\pm}$ fraction contained little or no uni-oligopotent HPCs, and a minority of multipotent and primitive HPCs, whereas it was dramatically enriched for HSCs. Conversely, the $CD34^+KDR^-$ fraction contained virtually all uni-oligopotent HPCs, as well as multilineage and primitive HPCs, and essentially no long-term repopulating HSCs.

In clonogenic semisolid culture, treatment of $CD34^+$ $KDR^+$ cells with VEGF, combined with diverse cocktails of hematopoietic growth factors (HGFs), caused a mild stimulatory effect on multipotent HPCs and primitive HPCs. More importantly, LDA of LTC-IC/CAFC frequency in the $KDR^+$ and $KDR^{31}$ cell fraction from PB, BM, or CB in Dexter type 12 week LTC revealed that, in PB, BM and CB $KDR^+$ cell fractions, the LTC-IC/CAFC frequency was elevated (approximately $\geq 50-60\%$, representative results) in LTC supplemented with VEGF, whereas it was lower (approximately 25–43%, representative results) in PB, BM and CB LTC which were not supplemented with VEGF. In both BM and CB $KDR^{31}$ cell fractions, the LTC-IC/CAFC frequency was 0% or close to 0% with or without VEGF treatment. Similar results on LTC-ICs/CAFCs were obtained in MPB $KDR^+$ cells. In preliminary experiments, twelve week incubation of normal PB $KDR^+$ cells with VEGF in single cell LTC, followed by seeding the generated cells into secondary LTC, caused an amplification of the number of HSCs, assayed as 12 week LTC-ICs. In addition, liquid suspension culture experiments on $CD34^+KDR^+$ vs $CD34^-$ $KDR^-CB$ cells confirmed that only the $KDR^+$ cell fraction generated in the long-term (approximately 12 week culture) primitive $CD34^+CD38^-$HPCs, particularly when stimulated by not only early acting HGFs (see below) but by VEGF combined with early acting HGFs. $CD34^+KDR^+$ cells seeded in single cell or minibulk $FCS^-$ free $HGF^-$ starvation culture partially survived for up to at least 1 month upon addition of VEGF. The starvation resistant cells were enriched for putative HSCs (up to approximately $\leq 80-95\%$, representative results).

These data therefore establish the following. VEGFRII (KDR) expression is restricted to a small subset of CB, BM, PB and MPB $CD34^+$ HPCs. This subset comprises virtually no uni- or oligopotent HPCs, a fraction of primitive HPCs and virtually the entire pool of long-term repopulating $CD34^+$ HSCs, respectively endowed with modest or extensive self-renewal capacity. Consistent with these results, VEGF selectively stimulates the proliferation of and/or protects against apoptosis primitive HPCs and particularly HSCs.

Furthermore, preliminary experiments suggest that $KDR^+$ cells in the $CD34^-lin^-$ cell population purified from adult hematopoietic tissues also contained a fraction of long-term repopulating HSCs. Therefore, the data disclosed herein demonstrate that KDR is novel key marker for human long-term repopulating HSCs and that the VEGF/KDR system plays a key role in long-term HSC function.

The Materials and Methods used in the experiments presented herein are now described.

VEGFRII (KDR) Antibody

The mouse monoclonal antibody (clone 260.4), raised against the KDR soluble protein and recognizing the extracellular KDR domain, was obtained tom Gesellschaft fur Biologische Forschung, GBF, Braunschweig, Germany.

Hematopoietic Growth Factors (HGFs)

Recombinant human HGFs were purchased from commercial sources (see below); VEGF was purchased from R&D Systems (Minneapolis, Minn.).

Cells and Purification Procedures

Human HPCs (containing a small HSC subpopulation), and the $KDR^+$ fraction thereof, were purified from (i) fetal liver (FL), (ii) cord blood (CB), (iii) adult bone marrow (BM), and (iv) adult normal or mobilized peripheral blood (PB, MPB), as described below.

$CD34^+$ Cell Purification

BM cells were obtained from consenting normal donors. MPB was obtained from G-CSF-treated (5 $\mu$g/kg/day) consenting normal donors. Normal PB was collected as buffy coat preparation from the local blood bank. CB was obtained from healthy, full-term placentas according to institutional guidelines. Low-density cells (<1.077 g/ml) were isolated by Ficoll and CD34$^+$ cells purified by MiniMACS column (Miltenyi Bergisch Gladbach, Germany and Auburn, Calif.).

Fluorescence Staining and Flow Cytometry Analysis

Purified CD34$^+$ cells were incubated for 30 min on ice with saturating amounts of biotinylated anti-KDR MoAb (clone 260.4, Gesellschaft fuir Biologische Forschung, Braunschweig, Germany) and anti-CD34 FITC MoAbs (clone HPCA-2, Becton-Dickinson (B-D), San Jose, Calif.). For three color FACS analysis, anti-CD34 PerCP and one of following FITC-conjugated MoAbs were used: anti-CD38 (B-D), anti-flt3 (Immunotech, Marseille, France), anti-Thy-1 (Pharmingen, San Diego, Calif.), anti-c-kit (Serotec, Oxford, UK). The cells were then washed and labeled with streptavidin-PE (B-D). After a further washing, cells were run on a FACScan or FACSCalibur for two- or three-color analysis.

CD34$^+$KDR$^+$ Cell Separation

Purified CD34$^+$ cells were incubated with saturating amounts of anti-CD34-FITC and biotinylated anti-KDR, washed and labeled with streptavidin-PE (B-D). After a further washing, CD34$^+$KDR$^+$ or KDR$^{+/\pm}$ and CD34$^+$KDR$^-$ subpopulations were sorted on FACSVantage (B-D) or EPICS Elite (Coulter) (fluorescence emission, 525 and 575 nm). A fraction of sorted KDR$^{31}$ cells was reanalyzed: if contaminating KDR$^+$ cells were detected, the population was restained and resorted to ensure elimination of all KDR$^+$ cells.

KDR RT-PCR was performed as described (Ziegler et al., 1999, Blood 93:3355–3368) using 5'-AAAACCTTTTGTTGCTTTTTGA-3' [SEQ ID NO:1] and 5'-GAAATGGGATTGGTAAGGATGA-3' [SEQ ID NO:2] primers (Terman et al., 1991, Oncogene 6:1677–1683).

In Vitro Assays

HPC Assay

HPCs were seeded in 0.9% methylcellulose fetal calf serum free (FCS$^-$) medium supplemented with saturating amounts of HGFs [flt3, kit ligand (FL, KL), basic fibroblast GF (bFGP) (100 ng/ml each), interleukin 6 (10 ng), IL3 (100 ), granulomonocyte colony-stimulating factor (GM-CSF) (10 ng), G-CSF (500 U), M-CSF (250 U), thrombopoietin (Tpo) (100 ng), erythropoietin (Epo) (3 U)]. CFU-Mix/BFU-E and CFU-GM colonies comprised >5×10$^3$ and >10$^3$ cells, respectively (Gabbianelli et al., 1995, Blood 86:1661–1670). A more limited HGF combination comprised IL3, GM-CSF, Epo at the indicated dosages (Gabbianelli et al., 1995, Blood 86:1661–1670) (this culture condition was also utilized for NOD-SCID mice BM rnononuclear cell (MC) clonogenic assay). CFU-Mix/BFU-E and CFU-GM colonies comrnprised >500 and >100 cells respectively. For detection of human colonies, The colony DNA was processed for PCR using KlenTaq-1 DNA polymerase (Clontech, Palo Alto, Calif.) and primers recognizing human a-satellie sequences on chromosome 17 (Warbunon et al., 1991, Genomics 11:324–333)

HPP-CFC Assay

HPP-CFC assay ws performed as described in Gabbianelli et al., (1995, Blood 86:1661–1670). Primary HPP-CFC clones, scored at day 30, were replated for secondary HPP-CFC colony formation.

Five-8–12-wk LTC

The LTC were established on allogeneic irradiated (20 Gy) BM stromas (Gabbianelli et al., 1995, Blood 86:1661–1670) or FBMD-1 cells (van der Loo et al., 1995, Blood 85:2598–2606). At weekly intervals half of the medium was removed and replaced by fresh medium±VEGF (100 ng/ml). In 12-wk LTC irradiated BM stromas or fresh FBMD-1 cells were added monthly to prevent functional exhaustion of the initial inoculum (Hao et al., 1996, Blood 88:3306–3313). In minibulk LTC each well was seeded with 100–1,000 CD34$^+$KDR$^+$ cells (1,000 cells/ml) (positive or negative control was seeded with 10,000 CD34$^+$ or CD34$^+$KDR$^{31}$ cells respectively). LTC were terminated at 5–8–12-wk: cells from supernatant and adherent fractions were cultured in semisolid medium for colony growth (Gabbianelli et al., 1995, Blood 86:1661–1670). Alternatively, 6–9–12-wk CAFCs were scored directly in LTC adherent layer (van der Loo et al., 1995, Blood 85: 2598–2606).

Limiting Dilution Assay (LDA)

Graded numbers of CD34$^+$KDR$^+$ cells (1–100 cells/well) were seeded in LTC wells (Sutherland et al., 1990, Proc. Natl. Acad. Sci. U.S.A. 87:3584–3588; Carè et al., 1999, Oncogene 18:1993–2001). The frequency of 12-week LTC-ICs/CAFCs was calculated according to single hit Poisson statistics (Sutherland et al., 1990, Proc. Natl. Acad. Sci. U.S.A. 87:3584–3588; Carè et al., 1999, Oncogene 18:1993–2001). Control LDA was performed on CD34$^+$KDR$^-$ cells (10–5,000 cells/well) and unseparated CD34$^+$ cells (20–5,000 cells/well).

Liquid Phase Suspension Culture

Liquid phase suspension culture in FCS$^-$ medium±VEGF and ±other HGFs was performed as in described in Ziegler et al. (1999, Blood 93:3355–3368). In the representative minibulk (2–3×10$^3$ CD34$^+$KDR$^{+/\pm}$ or CD34$^+$KDR$^{31}$ cells/well) or in single cell (1 CD34$^+$KDR$^{+/-}$ or CD34$^+$KDR$^-$ cell/well) starvation culture experiments, cells were treated only with VEGF (100 ng/ml). In a VEGF±HGFs representative experiment 1,000 purified CD34$^+$KDR$^+$ or CD34$^+$KDR$^-$ CB cells were grown in 100 μl of FCS-free medium (Gabbianelli et al., 1995, Blood 86:1661–1670) in individual wells of a 96-well plate until cell numbers reached approximately 10,000/well on or about day 14. Thereafter, the cells were transferred to individual wells of a 24-well plate with 500μl of medium. Cultures were supplemented with VEGF (50 ng/ml) either alone or combined with Tpo (100 ng/ml), FL (100 ng/ml), IL-3 (0.1 ng/ml). HGF combinations were VEGF alone, VEGF+FL, VEGF+FL+Tpo, VEGF+FL+IL-3, and FL+Tpo+IL-3. At weekly intervals, one half of the medium was replaced by fresh medium and HGFs. Starting at day 25 of culture, cell numbers were determined weekly and immunophenotype analysis of cultured cells was performed weekly using anti-CD34 and anti-CD38 MoAbs. The cultures were maintained for 12 weeks.

NOD-SCID Mice Xenografts

Six-8-week old mice (Jackson Laboratory, Bar Harbor, Me.) were irradiated at 3.5 Gy using a $^{137}$Cs source (Gammacell) 12–24 hours prior to xenotransplantation. KDR$^+$ or KDR$^{31}$ cells were injected by tail vein injection together with 100,000 irradiated (20 Gy) BM or CB mononuclear cells (MCs). Mice were killed 12 weeks after xenotransplantation according to institutional regulations. Cell suspensions from femurs, spleen and PB were analyzed for human cells by flow cytometry: erythrocytes depleted cells were labeled with FITC- or PE-conjugated MoAbs which specifically bound the following markers: CD45 (HLe1), CD34 (HPCA-2), CD38, CD15, CD33, CD71, CD2, CD3, CD4, CD7, CD8, CD19, CD20, CD16, CD56 (B-D); GPA, CD71 (Pharmingen, San Diego, Calif.). FITC- or PE-conjugated isotype-matched irrelevant MoAbs were used as controls. Bone marrow, spleen and PB cells from non-transplanted mice were used as negative control. Positive controls consisted of human BM or CB MCs. BMMCs were also cultured in semisolid media selective for human HPCs as described previously elsewhere herein.

Fetal Sheep Xenografts

Fetal sheep xenographs were performed as described previously (Zanjani et al., 1998, Exp. Hematol. 26:353–360; Civin et al., 1996, Blood 88:4102–4109; Kawashima et al., 1996, Blood 87:41364142; Sutherland et al., 1996, Exp. Hematol. 24:795–806; Uchida et al., 1996, Blood 88:1297–1305). PB and BM MCs from chimeric fetuses/newborns, separated by Ficoll gradient, were evaluated for presence of human cells by flow cytometry. BMMCs were also assayed for human HPCs in clonogenic culture by karyotyping of hematopoietic colonies. Human CD34$^+$ cells, isolated by MiniMACS column frDm BMMCs of primary recipients as described previously elsewhere herein, were transplanted in secondary recipients.

Receptor-type Tyrosine Kinases (RTKs) RT-PCR Assay in CD34$^+$KDR$^+$ Cells

BM CD34$^+$KDR$^+$ cells were isolated by double sorting and analyzed by RT-PCR (Ziegler et al., 1999, Blood 93:3355–3368). The following primers (Klagsbrun et al., 1996, Cytokine Growth Factor Rev. 7:259–270) were used for RT-PCR: VEGFRI/Flt1, 5'-AAACCAAGACTAGATAGCGTCA-3' [SEQ ID NO:3]; 5'-TTCTCACATAATCGGGGTTCTT-3' [SEQ ID NO:4]; VEGFRII/Flt4, 5'-GACAAGGAGTGTGACCACTGAA-3' [SEQ ID NO:5], 5'-TGAAGGGACATTGTGTGAGAAG-3' [SEQ ID NO:6]. The following primers (Sato et al., 1995, Nature 376:70–74), were also used: Tie1, 5'-GAGTCCTTCTTTGGGAGATAGTGA-3' [SEQ ID NO:7], 5'-GTCAGACTGGTCACAGGTTAGACA-3' [SEQ ID NO:8]; Tek, 5'-CATTTTTGCAGAGAACAACATAGG-3' [SEQ ID NO:9], 5'-TCAAGCACTGGATAAATTGTAGGA-3' [SEQ ID NO:10].

CD34$^-$lin$^-$ Cell Purification

Purification of CD34$^-$lin$^-$ cells was performed as indicated in Bathia et al. (Nature Med. 4:1038–1045). The KDR$^+$ cell subfraction of the CD34$^-$lin$^-$ cell fraction was obtained as indicated previously elsewhere herein for CD34$^+$cells.

The results of the Experiments presented herein are now described.

Figure 1B:
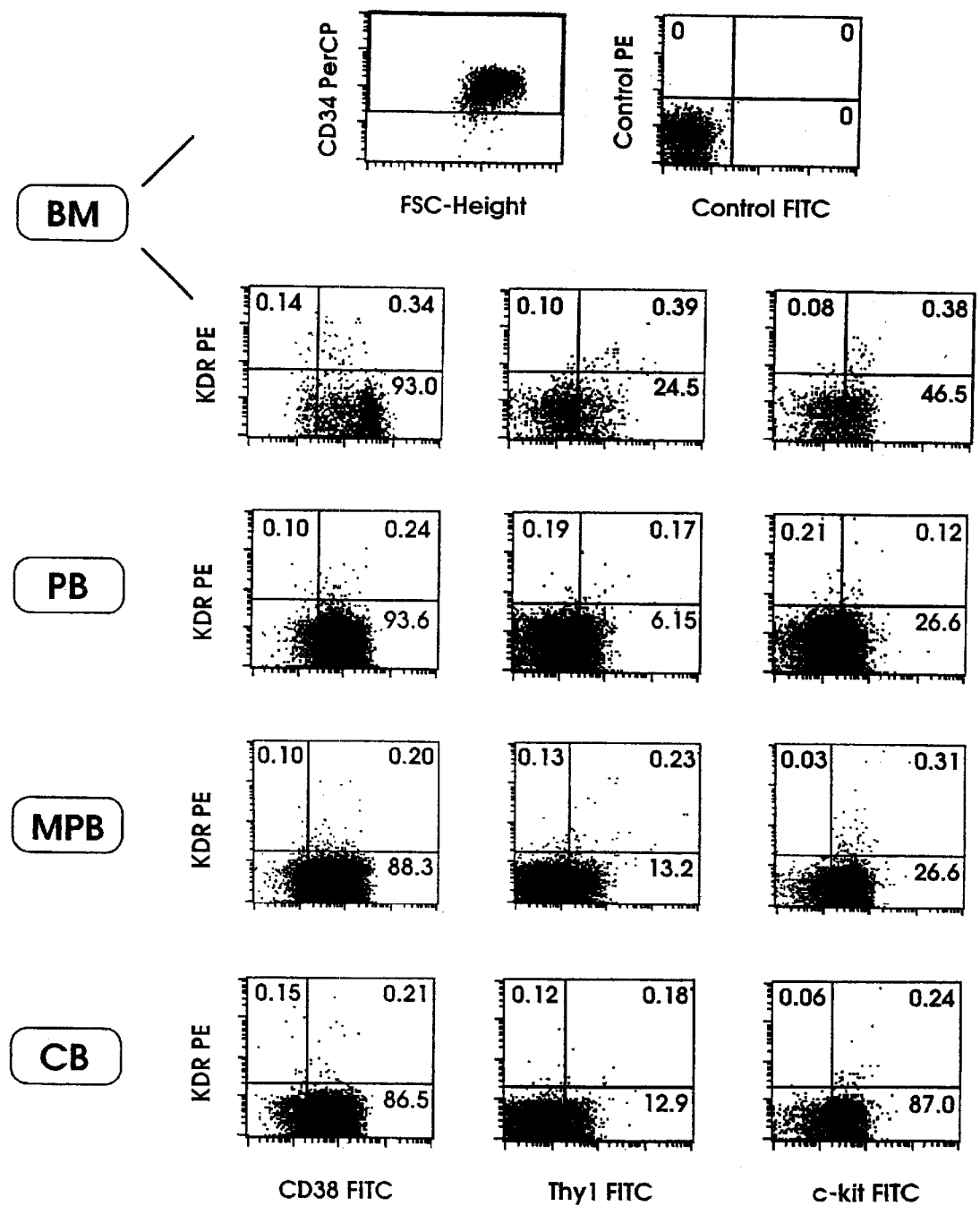
FIG. 1B is a graph depicting representative results on the expression of KDR and relevant early hematopoietic antigens in electronically gated CD34+ cells. Electronically gated CD34+ cells (top panels) from BM, PB, MPB, and CB were analyzed for expression of KDR and several early hematopoietic antigens, as indicated.

In preliminary studies, PB HPCs were purified and grown in unilineage differentiation cultures (Gabbianelli et al., 1990, Science 249:1561–1564; Testa et al., 1996, Blood 88:3391–3406). In accord with previous studies (Katoh et al., 1995, Cancer Res. 55:5687–5692), RT-PCR analysis confirmed that KDR mRNA was expressed in HPCs, but was not detected in the HPC progeny except for expression on megakaryocytes. Thereafter, a high-affinity monoclonal antibody (MoAb) which specifically binds the extracellular KDR domain was used to monitor KDR expression on HPCs from bone marrow (BM), normal peripheral blood (PB), mobilized peripheral blood (MPB), and cord blood (CB). Extensive FACS analysis on $\geq$98% purified CD34$^+$ cell populations from these tissues indicated that KDR$^+$ cells represent a minuscule subset of all CD34$^+$ cells, usually comprised in the <1% range (FIG. 1A, top panel) as confirmed by RT-PCR analysis (FIG. 1A, bottom right panel). A KDR$^\pm$ (KDR$^{dim}$) cell population has also been identified in CD34$^+$ cells (FIG. 1A, bottom left panel) and occasionally cosorted with the KDR$^+$ (KDR$^{bright}$) fraction. BM, PB, MPB, and CB CD34$^+$KDR$^+$ cells, essentially lin$^-$ (approximately <5–20% CD45RA$^+$, CD13$^+$, CD33$^+$, CD61$^+$, CD19$^+$in representative experiments), are variably positive for early HPC/HSC markers (FIG. 1B).

The hematolymphopoietic hierarchy is defined by functional assays. Pluripotent HSCs, endowed with extensive self-renewal capacity, are assayed in vivo on the basis of their capacity to repopulate the hematolymphopoietic system, i. e., to xenograft irradiated NOD-SCID mice (Bhatia et al., 1997, Proc. Natl. Acad. Sci. U.S.A. 94:5320–53–25; Wang et al., 1997, Blood 89:3919–3924; Conneally et al., 1997, Proc. Natl. Acad. Sci. U.S.A. 94:9836–9841) and pre-immune fetal sheep (Zanjani et al., 1998, Exp. Hematol. 26:353–360). HSCs feed into primitive HPCs endowed with limited self-renewal potential but extensive proliferative capacity, which are identified in vitro as high proliferative potential colony-forming cells, HPP-CFCs (Brandt et al., 1990, J. Clin. Invest. 86:932–941) and more advanced lineage(s)-committed HPCs with no self-renewal activity (defined in vitro as colony- or burst-forming units, CFUs, BFUs) (Ogawa, 1993, Blood 81:2844–2853).

The 5–8 week LTC identifies LTC initiating cells (LTC-ICs), which represent primitive HPCs apparently distinct from in vivo repopulating HSCs (Larochelle et al., 1996, Nature Med. 2:1329–1337). The 12 week extended LTC identifies more primitive LTC-ICs, which are resistant to retroviral gene transfer (Hao et al., 1996, Blood 88:3306–3313), as repopulating HSCs (Larochelle et al., supra), and represent putative HSCs. Similarly, the LTC identifies 5 week (van der Loo and Ploemacher, 1995, Blood 85:2598–2606) and 12 week cobblestone area forming cells (CAFCs). The data disclosed herein, utilizing the HSC/HPC functional assays, demonstrate that in post-natal hematopoietic tissues, KDR represents a specific functional HSC marker, which is virtually not expressed on oligo-, unipotent HPCs.

In Vitro HPC/HSC Assays

CD34$^+$KDR$^+$ cells were tested by in vitro HPC/HSC assays. Preliminary studies indicated that VEGF addition in CD34$^+$ cell culture exerts a mild stimulatory effect on multipotent CFU (CFU-Mix), HPP-CFCs and 8-wk LTC-ICs. Thereafter, CD34$^+$ cells were purified and the CD34$^+$KDR$^+$ or CD34$^+$KDR$^{+/\pm}$ subfractions were separated from the CD34$^-$KDR$^-$ subfraction (FIG. 1A, bottom left). Both subsets were then assayed for HPCs, HPP-CFCs and 6,9 and 12 week CAFCs or 5, 8, and 12 week LTC-ICs.

HPC Assay

Figure 2A:
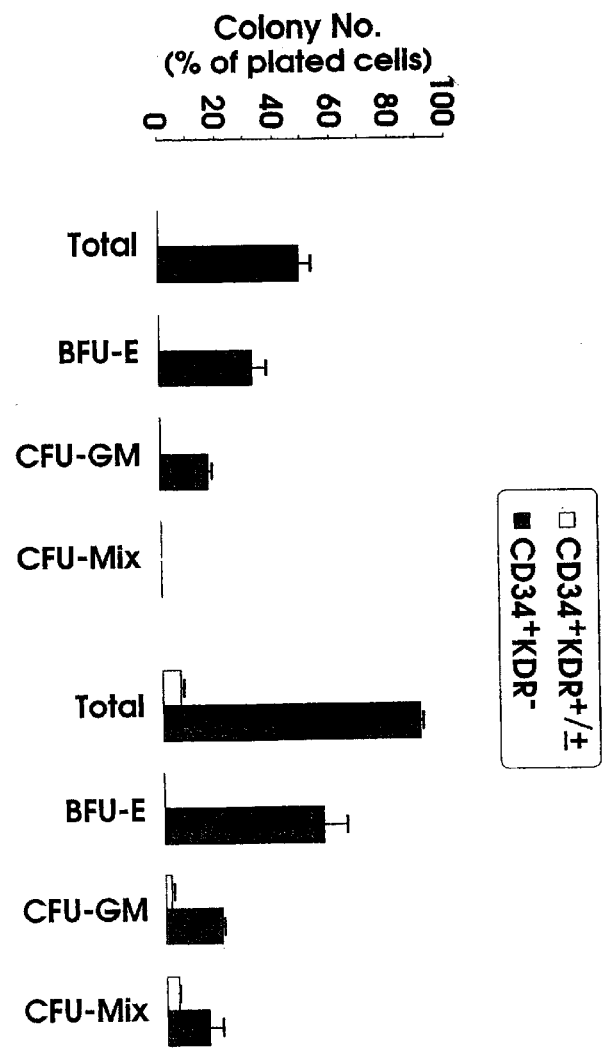
FIG. 2A is a graph depicting the in vitro HPC/HSC assays of CD34+KDR+ cells. Top panel depicts the HPCs in PB CD34+KDR+/± and CD34+KDR− cells assayed in cultures supplemented with a restricted (left) or large (right) spectrum of hematopoietic growth factors (HGFs). The bottom panels depict primary and secondary HPP-CFC colonies in PB CD34+KDR+ and CD34+KDR− cells. Mean±SEM from 4 independent experiments is disclosed.
Figure 2A:
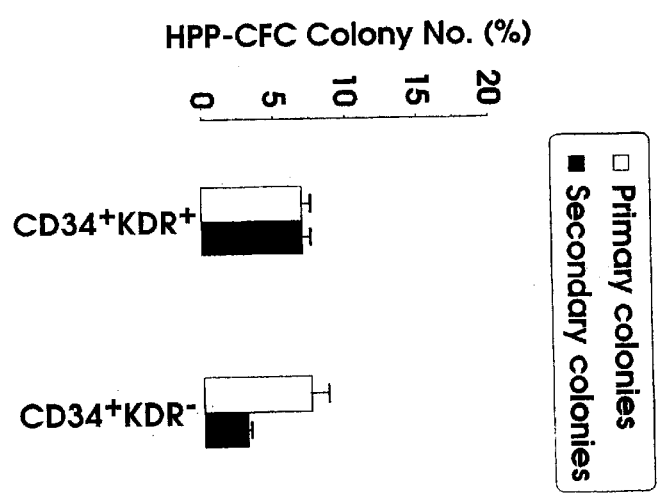

In representative PB experiments, the addition of saturating levels of interleukin 3 (IL3), granulomonocytic colony-stimulating factor (GM-CS F) and erythropoietin (Epo)

demonstrated that oligo-unipotent HPCs (BFU-E, CFU-GM) were essentially restricted to the KDR$^{31}$ cell fraction (FIG. 2A, top left). Addition of a larger spectrum of HGFs, i.e., including also early-acting HGFs c-kit ligand (KL), flt3 ligand (FL), IL6) as well as unilineage HGFs (thrombopoietin (Tpo), G-CSF, M-CSF), confirmed that virtually all oligo-unipotent HPCs are present in the KDR$^-$ fraction (FIG. 2A, top right). VEGF addition to the HGF cocktail did not modify this pattern, except for borderline increase of CFU-Mix in KDR$^+$ culture. Essentially similar results were obtained for CB, MPB and PB.

HPP-CFC Assay

HPP-CFCs scored in primary and secondary cultures (i.e., HPP-CFCs I and II, respectively) were present in both KDR$^+$ and KDR$^-$ fractions. The frequency of HPP-CFC II was more elevated in the KDR$^+$ fraction (<10%) as compared to the KDR$^-$ (<5%) population (FIG. 1B, bottom panel depicts PB results). Again, VEGF addition did not significantly modify this pattern, except for a slight increase of HPP-CFC number in the KDR$^+$ cell culture. Similar results were obtained for BM and CB.

LTC-IC/CAFC Assay

LTC-IC assay was performed in 5-, 8- and 12-week Dexter-type LTCs for CD34$^+$, CD34$^+$KDR$^{+/\pm}$, and CD34$^+$KDR$^{31}$ cells from BM, MPB, PB, and CB (see, e.g., FIG. 1C). The data disclosed demonstrate (FIG. 1C, left panel) that in LTC seeded with PB CD34$^+$ cells, the number of HPC generated declined sharply from 5 through 12 weeks, but a small residual number of HPCs was still detected at 12 weeks. In CD34$^+$KDR$^-$ LTC, a similar decline was observed, but no residual HPCs were detected at 12 weeks. Notably, CD34$^+$KDR+ LTC exhibited a moderately low number of HPCs at 5 and 8 weeks, followed by a sharp increase of HPC generation at 12 weeks. An equivalent pattern was observed in BM, MPB and CB LTC, as evaluated in 6, 9, and 12 week CAFC assay (FIG. 1C, middle and right panels).

Altogether, oligo-unipotent HPCs are essentially restricted to KDR$^-$ cells, while putative HSCs (12 week CAFCs/ LTC-ICs) are restricted to KDR$^+$ cells. The intermediate primitive HPC populations (HPP-CFCs, 6–9 week CAFCs, 5–8 week LTC-ICs) are present in both cell fractions.

NOD-SCID Mouse Assays

Irradiated NOD-SCID mice were transplanted with CD34$^+$(50,0000 to 250,000 cells/mouse), CD34$^+$KDR$^+$ or CD34$^+$KDR$^{+/\pm}$ (150 to 10,000 cells/mouse), or CD34$^+$KDR$^-$ (10,000 to 250,000 cells/mouse) from BM, CB, MPB or PB. In some experiments, CD34$^-$lin$^-$KDR$^+$ cells were also injected. Mice recipients were sacrificed at 12 weeks post-transplant and cell suspensions were obtained from BM, spleen and PB of mouse recipients and were analyzed by FACS for the presence of human cells as described elsewhere herein. Consistent engraftment was observed using CD34$^+$KDR$^+$ cells and essentially no engraftment was observed using double sorted CD34$^+$KDR$^-$ donor cells.

NOD-SCID Bone Marrow Studies

Figure 3A:
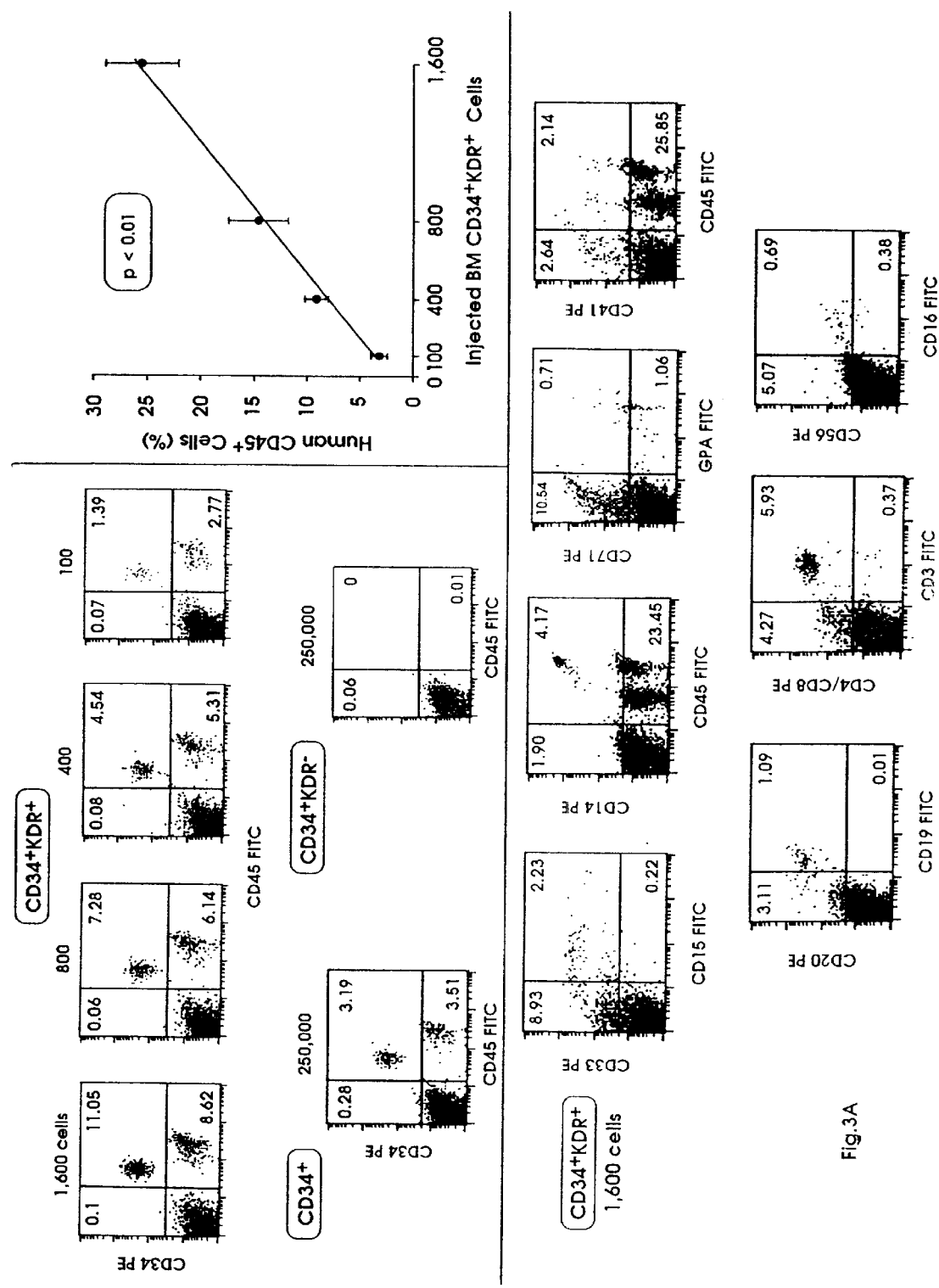
FIG. 3A is a graph depicting representative results on the engraftment of BM CD34+KDR+ cells in NOD-SCID mice demonstrating the repopulating activity of 100 to 1,600 CD34+KDR+ cells in recipient mice. The positive and negative controls received CD34+ and CD34+KDR$^{31}$ cells, respectively (top left). The top panels depict human CD34+/CD45+ cell engraftment (left top panel) and CD45+ cell dose-response (mean±SEM, three mice/group, r=0.99) (right top panel). Dose-dependent engraftment was also observed in recipient PB and spleen. The bottom panels depict the expression of human hematolymphopoietic markers in a representative mouse injected with 1,600 CD34+KDR+ cells.

In a representative experiment (FIG. 3A), between about 100 to about 1,600 CD34$^+$KDR$^+$ cells were injected into each NOD-SCID mouse recipient. In the negative control group, 250,000 double sorted CD34$^+$KDR$^{31}$ cells did not engraft, whereas unseparated CD34 cells demonstrated multilineage engraftment (FIG. 3A, top left panel). CD34$^+$KDR$^+$ cells always engrafted the recipient mouse. Moreover, the engraftment observed involved all hematopoietic lineages (i.e., double labeling for CD33$^+$15$^+$ or CD14$^+$45$^+$ cells, CD71$^{+GPA+}$ cells and CD45$^+$41$^+$ cells, pertaining to granulomonocytic, erythroid and megakaryocytic series, respectively) in representative mice (FIG. 3A, bottom panel). Further, the engraftment involved both B and T lymphoid compartments (i.e., CD19$^+$20$^+$ and CD4$^+$8$^+$3$^+$ cells, respectively), as well as NK cells (CD16$^+$56$^+$ cells) (FIG. 3A). A dose-response was observed from 100 through 1,600 cells for all engrafted cell populations (FIG. 3A, top), particularly for CD45$^+$ cells (FIG. 3A, top). Although T cell precursors require specific cognate interaction for maturation, human CD34$^+$CD4$^+$CD8$^+$ and CD3$^+$ CD2$^+$ cells were generated in NOD-SCID mice BM following injection of CD34$^+$CD38$^-$ cells (Bhatia et al., 1997, Proc. Natl. Acad. Sci. U.S.A. 94:5320–5325; Verstegen et al., 1998, Blood 91:1966–1976) or CD34$^-$lin$^-$ cells (Bhatia et al., 1998, Nature Med. 4:1038–1045). Also, in vitro experiments in the prior art indicate that the BM microenvironment is permissive for T cell development, and may recapitulate thymic maturation (Garcia-Ojeda et al., 1998, J. Exp. Med. 187:1813–1823). Further, without wishing to be bound by theory, the presence of contaminant mature human T cells in the transplanted CD34$^+$KDR$^+$ cells can be excluded in view of the lack of human T lymphocytes in mice receiving large numbers of CD34$^+$KDR$^{31}$ cells. Thus, the data disclosed herein demonstrate that human T cell precursors develop in BM of NOD-SCID mice. Taken together, these data establish that the CD34$^+$KDR$^+$ population, but not the CD34$^+$KDR$^-$ subset, is capable of establishing long-term (3 month) human hematopoiesis of the various hematopoietic lineages in NOD-SCID mice recipients.

NOD-SCID Cord Blood Studies

In five independent experiments, 200 to 15,000 CD34$^+$KDR$^+$ or 10,000 to 200,000 CD34$^+$KDR$^-$ CB cells were xenotransplanted into NOD-SCID mice. Human cells were virtually absent from mice transplanted with double sorted KDR$^-$ cells. In contrast, KDR$^+$ cells consistently generated human CD45$^+$ cells in BM, PB, and spleen of the recipient mice according to a dose-dependent pattern, e.g., representative results indicate that mice receiving 1,000 to 10,000 cells exhibited 27.2±7.1% (mean±SEM) human CD45$^+$ BM cells, whereas animals receiving 200 to about 800 cells demonstrated 3.75±1.5% CD45$^+$ BM cells. In a representative experiment, mice transplanted with 6,000 CD34$^+$KDR$^+$ cells (FIG. 3C) exhibited abundant BM human CD34 progenitors, precursors of the erythroid, granulomonocytic, and megakaryocytic lineages, as well as B and NK cells. The low CD3 expression detected may, without wishing to be bound by theory, reflect the low T cell generation potential of CB HSCs.

Multilineage Engraftment of Sheep Fetuses Using CD34$^+$KDR$^{+/+}$ Cells

BM studies involving CD34$^+$KDR$^+$ cells similar to those performed in NOD-SCID mice and disclosed previously herein were also performed in fetal sheep.

In a representative experiment, CD34$^+$ cells were purified from two human BM samples. The CD34$^+$KDR$^{+/\pm}$ or the CD34$^+$KDR$^-$ subfraction was then injected into the preimnmune fetuses of eight pregnant ewes. The primary recipients received CD34$^+$KDR$^{+/\pm}$, CD34$^+$KDR$^{31}$ , or CD34$^+$ cells (four, three and two fetuses per group, respectively) and the recipients were then sacrificed on day 60 post-transplant. Other fetuses injected with CD34$^+$KDR$^{+/\pm}$ or with CD34$^+$KDR$^{31}$ cells were born. In addition, human CD34$^+$ cells from primary fetuses treated with KDR$^{+/\pm}$ cells were transplanted into secondary fetuses (Kawashima et al., 1996, Blood 88:4136–4142; Civin et al., 1996, Blood 88:4102–4109).

Figure 4:
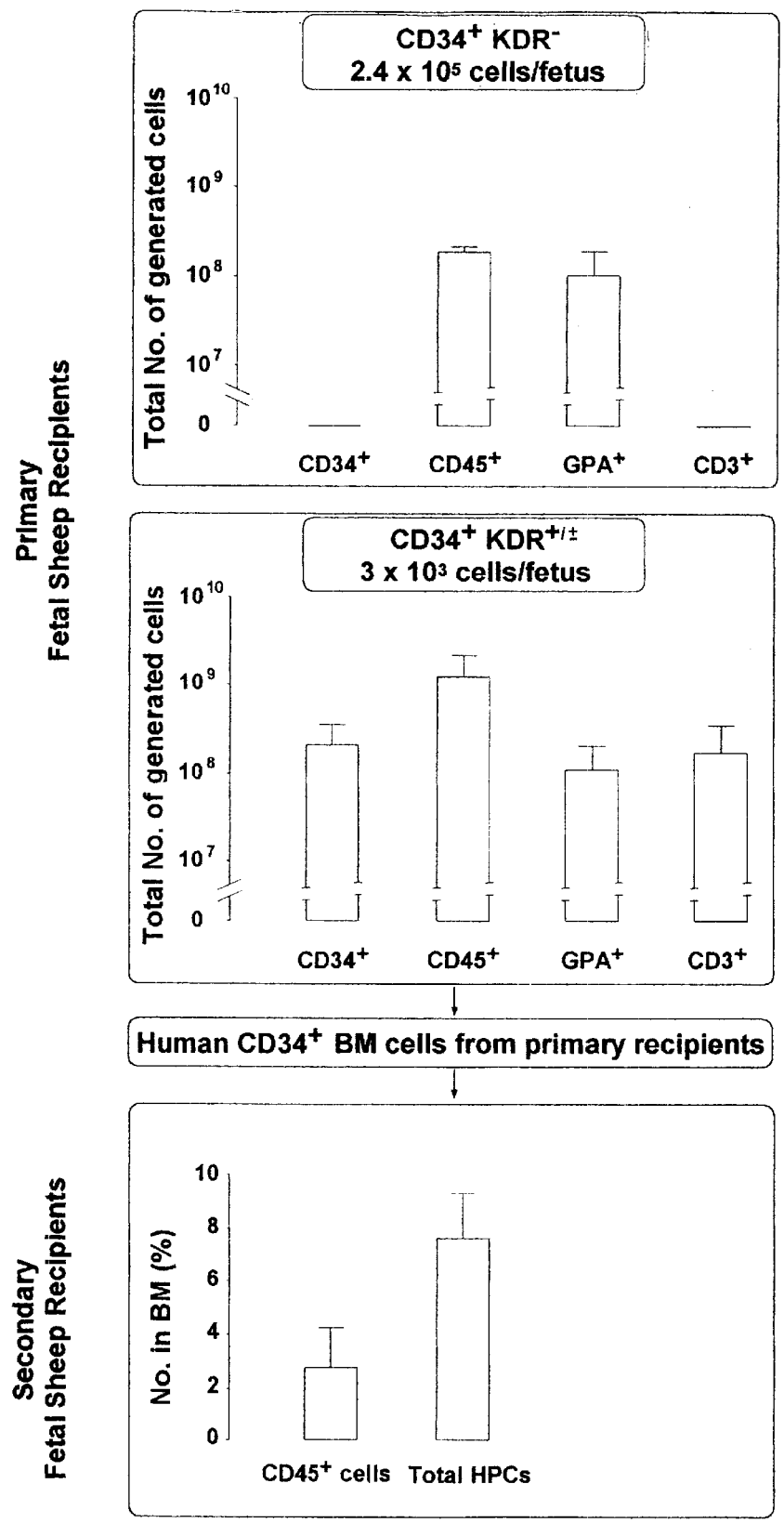
FIG. 4 is a graph (comprising three panels) depicting representative results on the engraftment of BM CD34+KDR+ cells in primary and secondary fetal sheep. The total estimated number of human CD34+, CD45+, glycophorin A+ (GPA+), and CD7+ cells generated in primary fetal sheep recipients transplanted with CD34+KDR+/± (middle panel) or CD34+KDR$^{31}$ cells top panel) (mean±SEM). The percentage of human CD45+ cells and total HPCs in BM of secondary sheep fetuses is depicted in the bottom panel (mean±SEM).

In primary fetal sheep recipients, transplantation of 1.2×10$^5$ CD34$^+$ cells per fetus consistently induced engraftment; that is, BM analysis indicated the presence of a significant fraction of differentiated (0.30% CD45$^+$ cells, mean values) and undifferentiated (0.17% CD34$^+$ cells) hematopoietic precursors. Further, clonogenic assay demonstrated that 6.8% CFU-Mix/BFU-E and 5.2% CFU-GM of all scored colonies were of human origin. A small number (3×10$^3$ cells/fetus) of CD34$^+$KDR$^{+/\pm}$ cells consistently engrafted with an impressive multilineage expression for the differentiated compartments: 1.78% CD45$^+$, 0.16% GPA$^+$, and 0.34% CD3$^+$ cells. Further, these fetuses exhibited a consistent engrafment with multilineage expression for the undifferentiated compartment: 0.32% CD34$^+$. Within the HPC pool, the frequency of human HPCs was elevated, i.e., 9.3% for CFU-Mix/BFU-E and 16.2% for CFU-GM of all scored colonies were of human origin. An 80-fold larger number (2.4×10$^5$ cells/fetus) of CD34$^+$KDR$^{31}$ cells did not engraft any fetus, as indicated by the consistent absence of CD34$^+$ and CD3$^+$ cells. Moreover, only a small percentage of differentiated hematopoietic precursors was detected (i.e., 0.7% CD45 cells), together with a few late CFU-GM (2.4%) giving rise to small colonies. It is estimated that an approximate total of greater than 10$^8$ CD34$^+$ and CD3$^+$ human cells were generated per fetus by KDR$^+$ cells, whereas no CD34$^+$ and CD3$^+$ cells were generatedby KDR$^{31}$ cells (FIG. 4, middle and top panels).

Each secondary fetal sheep recipient received 4×10$^5$ human BM CD34$^+$ cells, derived from the primary fetuses originally transplanted with KDR$^{+/\pm}$ cells. After two months, the four secondary recipients were sacrificed and all demonstrated multi-lineage engraftment (FIG. 4, bottom).

In born sheep recipients at three weeks after birth, both sheep transplanted with KDR cells in fetal life exhibited persistent multilineage engraftment at the BM level. One sheep featured an extremely abundant progeny of human CD45$^+$ cells and 8.8% colonies of human origin, and the other sheep exhibited 1.0% CD45$^+$ cells (the colony number was not evaluated for this sheep due to bacterial contamination of the culture plates).

These representative fetal sheep results, confirmed in other experiments, indicate that the CD34$^+$KDR$^{+/\pm}$ fraction is enriched for HSCs giving rise to multilineage engraftment in primary/secondary fetuses and born sheep. The engraftment in secondary recipients is noteworthy. Indeed, positive results in secondary fetal recipients successfully compare with those observed by follow up to primary transplanted fetuses for long periods after birth (Civin, 1996, Blood 88:4102–4109). On the other hand, the CD34$^+$KDR$^-$ fraction does not engraft and contains only HPCs giving rise, in primary recipients, to differentiated hematopoietic precursors and a few late CFU-GM.

In sum, the data disclosed herein regarding the NOD-SCID and fetal sheep xenotransplantation assays indicate that restriction of HSCs to the KDR$^+$ subfraction of CD34$^+$ cells. Previous studies in NOD-SCID mice and in sheep fetuses demonstrated that HSCs are enriched in diverse CD34$^+$ cell subfractions, e.g., CD38$^-$ (Bhatia et al., 1997, Proc. Natl. Acad. Sci. U.S.A. 94:5320–5325; Wang et al., 1997, Blood 89:3919–3924; Conneally et al., 1997, Proc. Natl. Acad. Sci. U.S.A. 94:9836–9841; Verstegen et al., 1998, Blood 91:1966–1976; Civin et al., 1996, Blood 88:4102–4109), kit$^{low}$ (Kawashima et al., 1996, Blood 87:4136–4142), Thy-1$^+$ (Sutherland et al., 1996, Exp. Hematol. 24:795–806), and Rhodamine (Rh)$^{dim}$ (Uchida et al., 1996, Blood 88:1297–1305). However, engraftment was also observed at a lower level for the complementing subfractions, i.e., CD38$^+$ cells (Conneally et al., 1997, Proc. Natl. Acad. Sci. U.S.A. 94:9836–9841; Verstegen et al., 1998, Blood 91:1966–1976; Civin et al., 1996, Blood 88:4102–4109), kit$^-$ (Kawashima et al., 1996, Blood 87:4136–4142), Thy-1$^-$ (Sutherland et al., 1996, Exp. Hematol. 24:795–806), and Rh$^{bright}$ (Uchida et al., 1996, Blood 88:1297–1305).

Figure 3B:
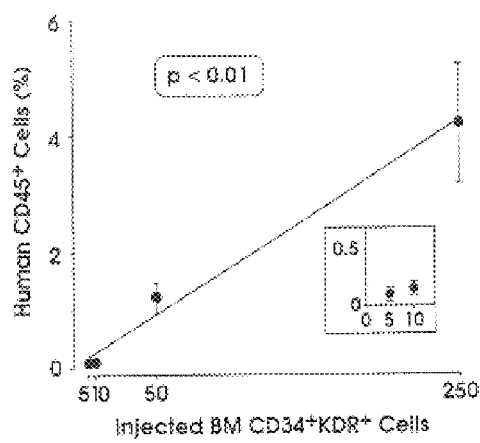
FIG. 3B is a graph depicting representative results on the engraftment of BM CD34+KDR+ cells in NOD-SCID mice demonstrating the LDA of repopulating HSC frequency in CD34+KDR+ cells. Graded numbers of BM CD34+KDR+ cells were injected into recipient mice. The positive and negative controls received CD34+ and CD34− KDR$^{31}$ cells, respectively. The top panels depict human CD45+ cells in BM of mice injected with 250, 50, 10 or 5 cells (3, 9, 6 and 6 mice per group, respectively) (mean±SEM). The bottom left panel depicts human HPCs in BM of the 4 engrafted mice injected with 5 cells (mean±SEM) (left) and the LDA according to single hit Poisson statistics (right). The bottom right panel depicts the PCR analysis of human alpha-satellite DNA (867 bp band) in all scored colonies from a representative mouse that received 5 cells. The contents of the lanes are indicated in the figure, in addition lane 13 depicts a human DNA positive control, lane 14 depicts a no DNA template negative control, lane 15 comprises DNA from BM mononuclear cells of a nontransplanted mouse and M.W. indicates a lane comprising molecular weight markers.
Figure 3B:
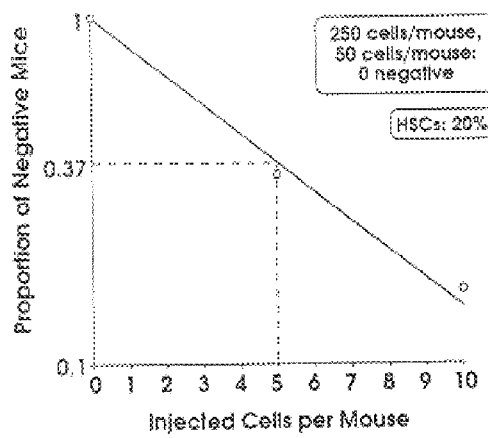
Figure 3B:
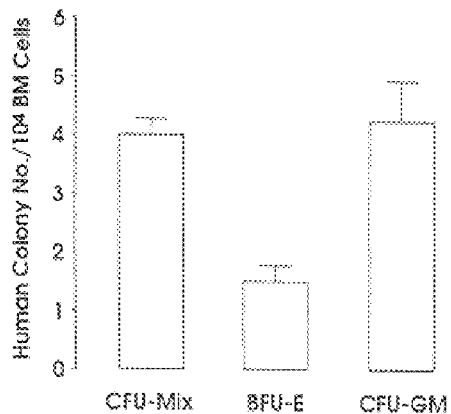
Figure 3B:
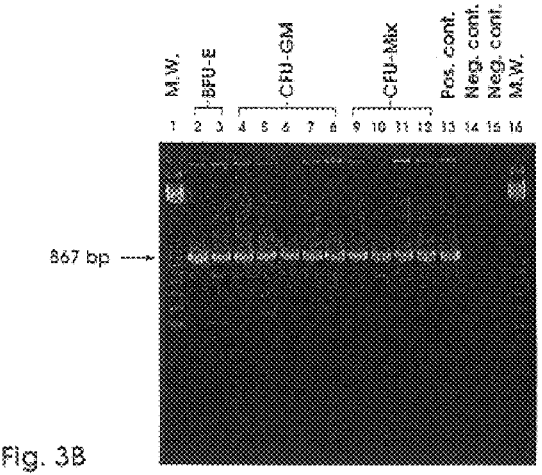
Figure 3C:
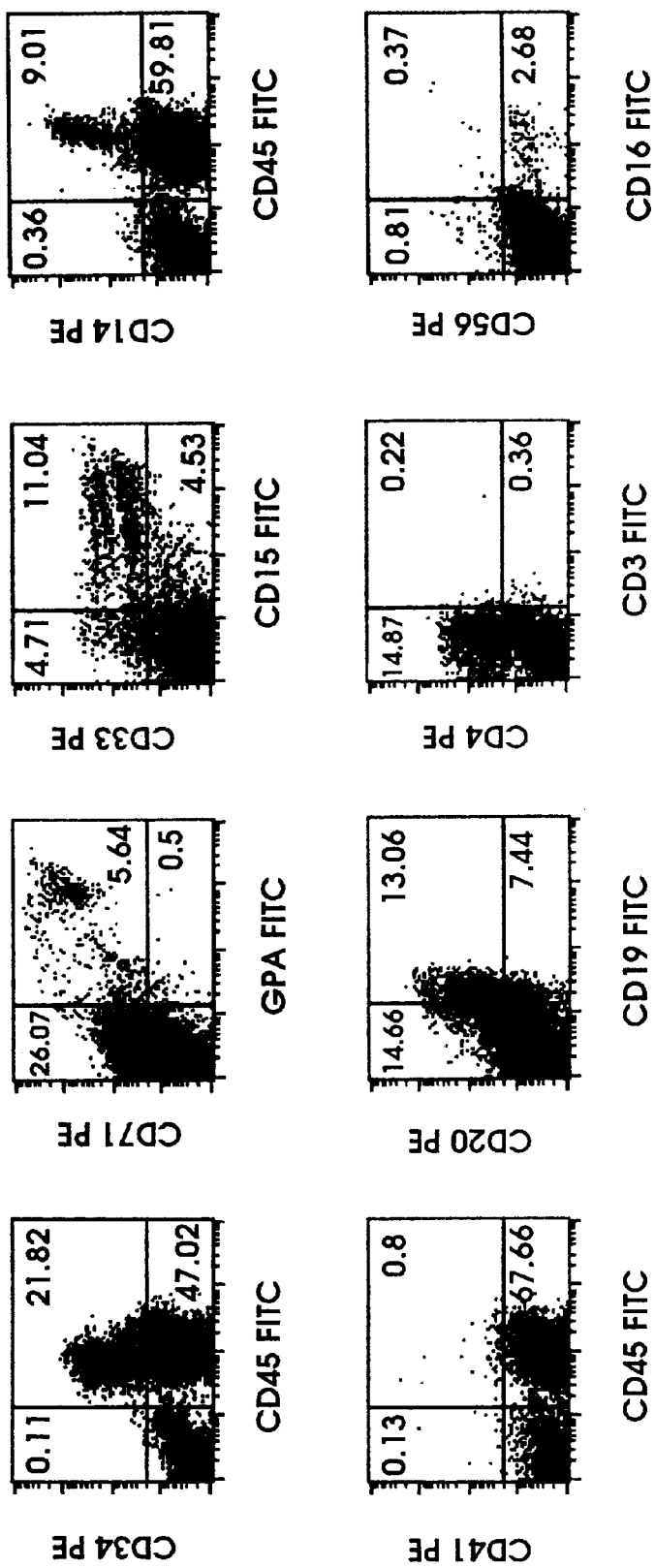
FIG. 3C is a graph depicting the expression of informative human hematolymphopoietic markers in a representative mouse receiving 6,000 CB CD34+KDR+ cells as described elsewhere herein.

Frequency of Repopulating HSCs and 12-week CAFCs/LTC-ICs in CD34$^+$KDR$^+$ Cell Fraction In NOD-SCID mice injected with from about 100 to about 1,600 BM CD34$^+$KDR$^+$ cells, the representative CD45$^+$cell dose-response (FIG. 3A) indicated that a cell number far lower than 100 cells would successfully engraft. Therefore, a representative LDA was performed using 250, 50, 10 or 5 BM CD34$^+$KDR$^+$ cells/mouse (FIG. 3B). After injection of 250 to 5 BM KDR$^+$ cells, a dose-dependent multilineage engraftment was detected (FIG. 3B, top and bottom left). All mice were repopulated by 250 and 50 cells, while five of six mice injected with 10 cells and four of 6 mice injected with 5 cells were engrafted based on flow cytometry analysis (FIG. 3B, top left) and HPC assay validated by PCR of human a-satellite DNA in the scored colonies (FIG. 3B, bottom). LDA indicated an approximately 20% frequency value for repopulating HSCs in CD34$^+$KDR$^+$ cells (FIG. 3B, top right). This representative value is similar to the representative 25% CAFC frequency exhibited in VEGF$^-$ BM LTC, indicating that repopulating HSCs and 12 week LTC-ICs/CAFCs are closely related.

Figure 2B:
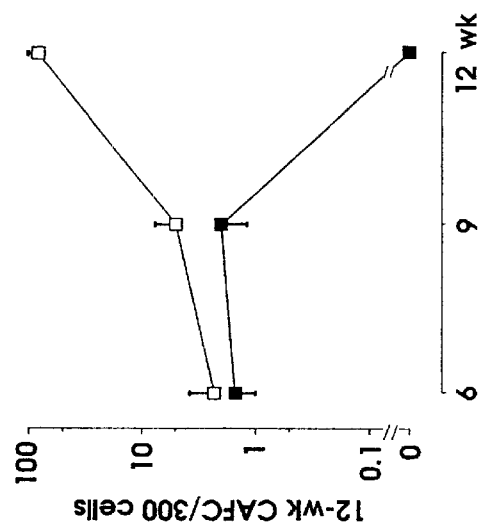
FIG. 2B is a graph depicting the PB CD34+, CD34+KDR−, and CD34+KDR+/± cell LTC (left panel): at 5, 8, and 12 weeks, supernatant and adherent cells were assayed for HPCs. The middle and right panels depict BM (middle) and CB (right) CD34+KDR$^{31}$, CD34+KDR+ cell LTC analyzed for CAFC-derived colonies at 6, 9, and 12 weeks. Mean±SEM from three experiments is disclosed.
Figure 2B:
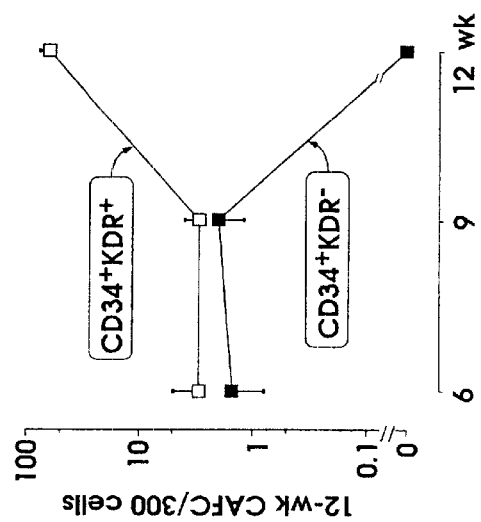
Figure 2B:
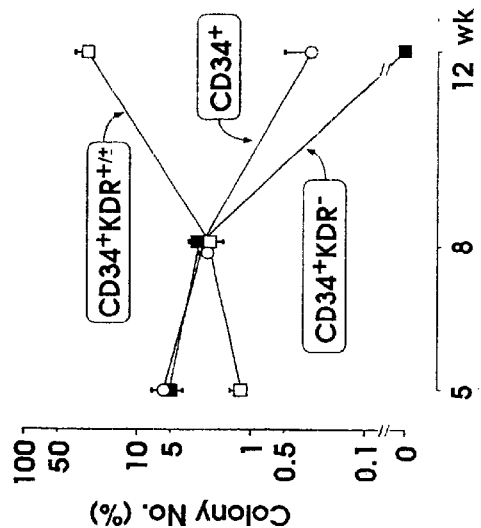
Figure 2C:
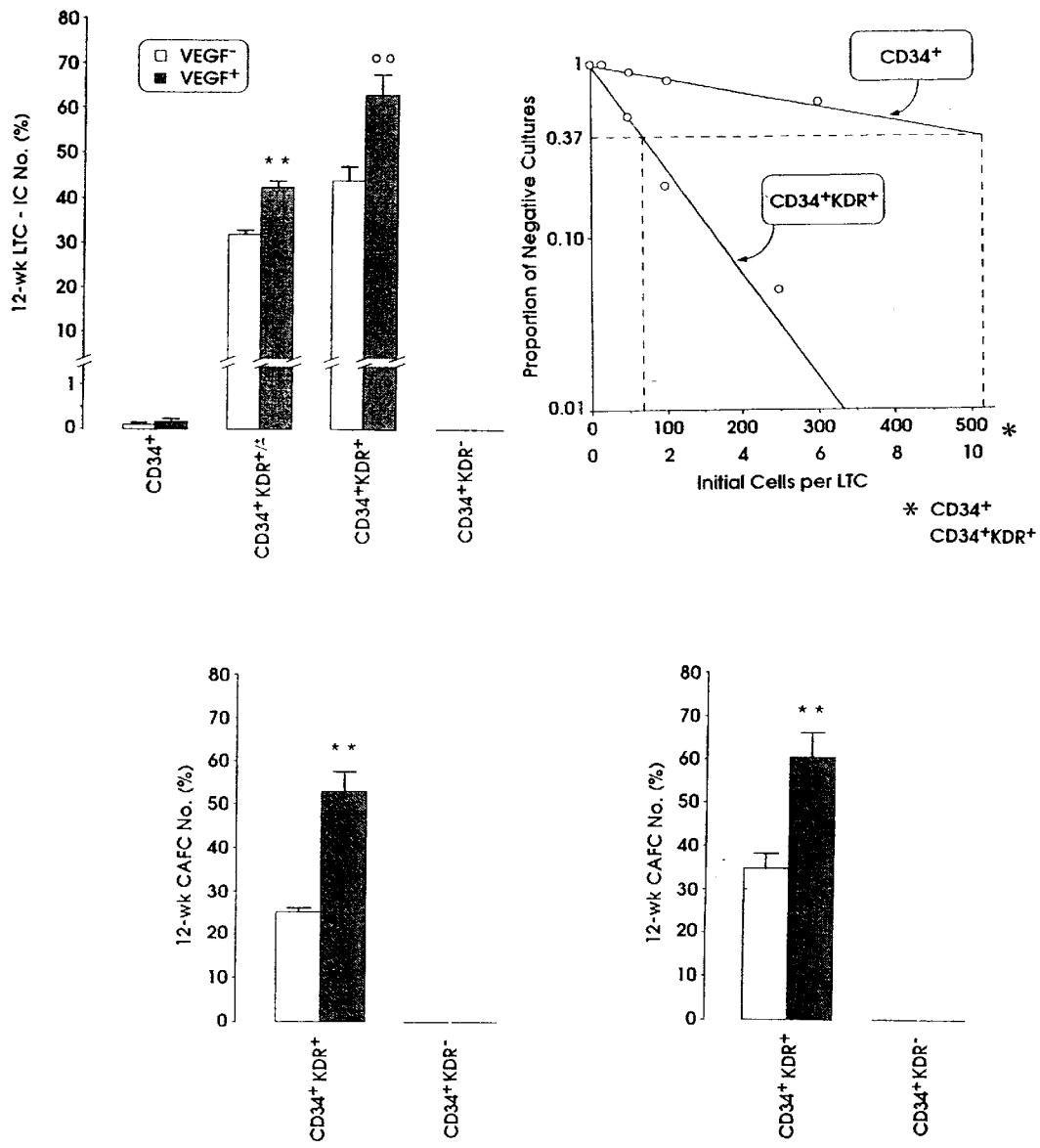
FIG. 2C is a graph depicting LDA of 12 week LTC-ICs/CAFCs in CD34+KDR+ cells. The top left panel depicts LTC-IC frequency in PB CD34+, CD34+KDR+/±, CD34+KDR+, and CD34+KDR− cells. The mean±SEM for five separate VEGF+ or three separate VEGF− experiments is shown. The top right panel depicts representative LDAs for PB CD34+ and CD34+KDR+ cells (100 replicates for the lowest cell concentration (e.g., 1 KDR+ cell) and decreasing replicate numbers for increasing cell concentrations, i.e., 50, 20, 10 wells with 2, 5, 10 KDR+ cells, respectively. The bottom panels depict CAFC frequency in KDR+ and KDR$^{31}$ cells from BM (left) or CB (right). The mean±SEM for three separate experiments is shown. The ** indicates that p<0.01 when compared to the VEGF− group. The symbol °° indicates that p<0.01 when compared to the other groups.

In representative experiments on 12 week extended LTCs treated or not with VEGF, LDA indicated that the CAFC frequency in CD34$^+$KDR$^+$ cell of BM (FIG. 2B, left) or CB (FIG. 2B, right) CAFC is lower in VEGF$^-$ (approximately 25–35%) than in VEGF$^+$ (approximately 53–61%) LTC. No CAFC were detected in CD34$^+$KDR$^{31}$ cell fractions.

Representative corresponding experiments on LTC-IC frequency in CD34$^+$KDR$^-$ or CD34$^+$KDR$^+$ fractions from BM, CB, MPB and PB showed a pattern similar to that observed for CAFC frequency.

The 20% repopulating HSCs frequency in CD34$^+$KDR$^+$ BM cells was about 100–150-fold more elevated than the frequency reported in CD34$^+$CD38$^-$ BM or CB cells (Bhatia et al., 1997, Proc. Natl. Acad. Scid. U.S.A. 94:5320–5325; Wang et al., 1997, Blood 89:3919–3924; Conneally et al., 1997, Proc. Natl. Acad. Sci. U.S.A. 94:9836–9841). It is noteworthy that in representative experiments the CD34$^+$CD38$^-$ fraction comprises about 1–2% KDR$^+$ cells. This result explains the different HSC frequency in the CD34$^+$38$^-$ subset compared to the frequency in the CD34$^+$KDR$^+$ cell subset. The assay performed herein lasted for 3 months and the mice were not treated with cytokines, whereas in other studies the assay usually lasts 1.5 to 2 months and often involves cytokine treatment (Larochelle et al., 1996, Nature Med. 2:1329–1337).

Representative in vitro LDAs indicated that 25 to 35% CAFCs were present in BM and CB CD34$^+$KDR$^+$ cells, as evaluated in VEGF$^-$ 12-week LTC. Without wishing to be bound by theory, since the CAFC frequency rises to 53 to 63% in these representative VEGF+LTCs, it is predicted that the in vivo repopulating HSC frequency will be more elevated in mice injected with human VEGF±with or without other cytokines. Importantly, the significant increase of CAFC/LTC-IC frequency induced by VEGF addition suggests that VEGF exerts a key proliferative and/or anti-apoptotic effect on putative HSCs.

Increased 12 Week CAFC/LTC-IC Frequency in Starvation Resistant $CD34^+KDR^+$ Cells The 12 week LTC-IC frequency in starvation resistant $CD34^+KDR^+$ or $CD34^+KDR^{+/\pm}$ cells was examined. In representative experiments, $CD34^+KDR^+$ or $CD34^+KDR^{+/\pm}$ and $CD34^+KDR^{31}$ cells were seeded into $FCS^-$ free liquid suspension minibulk cultures, supplemented with VEGF but deprived of other HGFs. The $KDR^+$ or $KDR^{+/\pm}$ cell number decreased sharply in the first five days of culture, but then leveled down to 10–25% residual cells through day 30. Conversely, all $KDR^{31}$ cells were dead at day 10 of culture. In single $CD34^+KDR^+$ cell starvation cultures not supplemented by VEGF all cells died while approximately 20% of cells treated with VEGF survived (FIG. 2D, top), indicating the key anti-apoptotic effect of VEGF on this cell type.

Figure 2D:
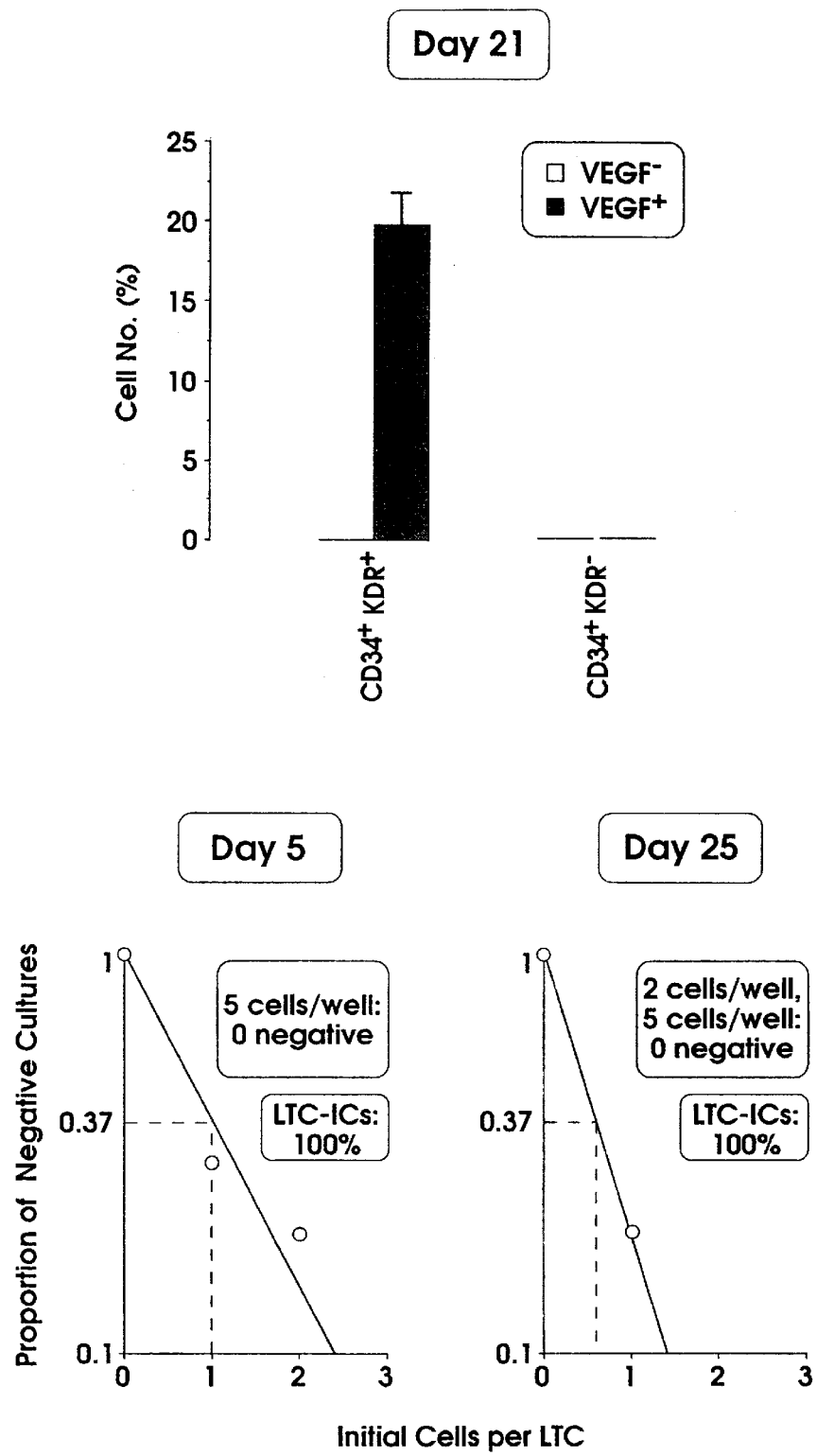
FIG. 2D is a graph depicting the starvation of PB CD34+KDR+/±, or CD34+KDR$^{31}$ cells in single cell FCS− free liquid phase culture supplemented or not with VEGF (top): the percentage of cells that survived at day 21 (mean±SEM from 3 separate experiments) is shown. The bottom panels depict the minibulk (2×10$^3$ cells/ml) PB CD34+KDR+/± starvation culture supplemented with VEGF: the limiting dilution assay (LDA) of LTC-IC frequency in the approximately 25% cells surviving on day 5 and 25 is shown.

The starvation resistant $KDR^{+/\pm}$ fraction contained virtually no multipotent/primitive HPCs (CFU-Mix/HPP-CFC assays), but exhibited an elevated 12 week LTC-IC frequency, approximately ≧80–95% at day 5–30 (FIG. 2D, bottom panels). Control $KDR^{31}$ cells never contained 12 week LTC-ICs. Without wishing to be bound by theory, based on the similarity between in vivo and in vitro HSC assay results, it may be that the starvation-resistant $CD34^+KDR^+$ cells represent HSCs having in vivo long-term repopulating capacity. The data disclosed herein are in accord with prior studies demonstrating that one of the key features of adult HSCs is their quiescent status in a prolonged cell cycle (Ogawa, 1993, Blood 81:2844–2853; Morrison et al., 1997, Cell 88:287–298; Orlic and Bodine, 1994, Blood 84:3991–3994). That is, the high frequency of HSCs in $CD34^+KDR^+$ cells capable of withstanding serum starvation may be due to their ability to remain quiescent which is a known characteristic of adult HSCs thus further suggesting that $KDR^+$ is a marker specific for HSCs.

HSCs in $CD34/lin^-/KDR^+$ Cells

Experimental and clinical observations leave little doubt that human HSCs with long-term engrafting ability are $CD34^+$ (Berenson et al., J. Clin. Invest. 81:951–955; Berenson et al., 1991, Blood 77:1717–1722; Bensinger et al., 1996, Blood 88:4132–4138). This has also been confirmed not only in the SCID mouse models, but also in the sheep models where $CD34^+$ cells have caused engraftment lasting >5 years (Zanjani et al., 1996, Int. J. Hematol. 63:179–192). However, recent studies in both mice (Osawa et al., 1996, Science 273:242–245; Goodell et al., 1996, J. Exp. Med. 183:1797–1806) and rhesus monkeys (Johnson et al., 1996, Blood 88:629a) have demonstrated the $CD34^-$ cells population contain progenitors capable of producing $CD34^+$ cells in vitro and to be highly enriched in HSCs with competitive long-term in vivo repopulating potential.

Recent reports (Zanjani et al., 1998, Exp. Hematol. 26:353–360; Almeida-Porada et al., 1998, Exp. Hematol. 26:749) suggest that in the sheep fetus large numbers ($>10^5$) of human BM $CD34^-$ cells can engraft.

Furthermore, studies by Bhatia et al. (1998, Nature Med.4:1038–1045) indicate that $1–2\times10^5$ BM or CB $CD34^-$ $lin^-$ cells engraft a majority of NOD-SCID mice after 2–3 months, with generation of $CD34^+$ cells and multilineage expression including B and T lymphocytes. The data disclosed herein demonstrate that NOD-SCID mice injected with 4,000 $CD34^-lin^-KDR^+$ CB cells consistently exhibited $CD34^+$ cell generation and multilineage engraftment after three months. Specifically, the following representative values were detected in BM: 0.19% $CD34^+$ and 0.11% $CD34^+$ $CD45^+$ cells, coupled with multilineage expression (e.g., 0.23% $CD45^+$, 0.18% $CD33^+$, 0.10% $CD15^+$, 0.27% $GPA^+$, 0.27% $CD71^+$, 0.15% $CD20^+$, 0.12% $CD19^+$, 0.25% $CD3^+$, and 0.11% $CD56+CD16^+$). In the same experiment, 4,000 $CD34^-KDR^+$ cells engrafted. Furthermore, 10,000 $KDR^+$ CB mononuclear cells engrafted, whereas 100,000 $KDR^-$ CB mononuclear cells did not engraft.

A large number of human BM and CB $CD34^-lin^-$ cells engraft fetal sheep and NOD-SCID mice, as indicated by multilineage expression and generation of a $CD34^+$ cells. Approximately one percent or less of $CD34^-/lin^-$ cells are $KDR^+$ Indeed, a discrete number of CB $CD34^-lin^-KDR^+$ cells engraft NOD-SCID mice and generate $CD34^+$ cells. Based on these results, and without wishing to be bound by theory, KDR is a key marker for $CD34^-$ HSC in post-natal life.

Although HSCs have previously been enriched in diverse $CD34^+$ cell subsets, a HSC defining marker had not, prior to the present invention, been identified. The data disclosed herein demonstrate that the $CD34^+KDR^+$ cell fraction has novel properties. HSCs are essentially restricted to this population, whereas oligo-unipotent HPCs are virtually restricted to $CD34^+KDR^{31}$ cells. Further, the HSC enrichment in $CD34^+KDR^+$ cells is strikingly elevated, i.e., the putative HSC frequency rises to ≧80–95% in starvation resistant $CD34^+KDR^+$ cells. Altogether, these results indicate that KDR is a novel functional marker defining HSCs.

Purification of $CD34^+$HPCs has markedly facilitated studies on early hematopoietic precursors (Ogawa et al., 1993, Blood 81:2844–2853; Gabbianelli et al., 1990, Science 249:1561–1564). The isolation of $KDR^+$ HSCs offers a unique opportunity to elucidate the cellular/molecular phenotype and functional properties of HSCs/HSC subsets. These issues, exceedingly elusive so far, are of pivotal significance for a large array of biotechnological and clinical aspects, e.g., autologous/allogeneic HSC transplantation, in vitro blood cell generation for transfusion medicine, and HSC gene therapy in hereditary/acquired hematology-immunology disorders.

The data disclosed herein shed light on recent studies on embryonic hematoangiogenesis. Studies on $Flk-1^{-/-}$ knock out mice (Shalaby et al., 1997, Cell 89:981–990) indicate that Flk- I is required to initiate both primitive and definitive hematolymphopoiesis, as well as vasculogenesis. These data suggest a role for Flk-1 in generation of hemoangioblasts, i.e., putative stem cells for both hematolymphopoietic and endothelial lineages (Flamme et al., 1992, Development 116:435–439). $Flk-1^+$ and $CD34^+$ cells are present in murine embryonic-fetal liver (Kabrun et al., 1997, Development 124:2039–2048). In differentiating embryonic stem cells, embryoid bodies treated with VEGF and KL give rise to $CD34^+$and $flk-1^+$ blast cell colonies, which generate secondary colonies composed of all hematopoietic lineages (Kennedy et al., 1997, Nature 386:488–492) and which also exhibit endothelial developmental capacity (Nishikawa et al., 1998, Development 125:1747–1757; Choi et al., 1998, Development 125:725–732).

Altogether, previous studies suggested the existence of embryonic $CD34^+flk-1^+$ hemoangioblast, but did not provide evidence for a prenatal CD34⁺flk-1⁺ repopulating HSC. The data disclosed herein demonstrate the existence of post-natal CD34⁺KDR⁺ repopulating HSC. Without wishing to be bound by theory, taking together the data disclosed herein, KDR-flk-1 may hypothetically define both post-natal and pre-natal HSCs/hemoangioblasts.

Recently, bone marrow-derived cells have been demonstrated to give rise to hepatic oval cells, which can differentiate into the other two types of epithelial cells in the liver, i.e., ductular cells and hepatocytes (Petersen et al., 1999, Science 284:1168–1170). In addition, bone marrow-derived cells have been demonstrated to have the capability to give rise to myogenic progenitors (Ferrari et al., 1998, Science 279:1528–1530). Also, bone marrow-derived were induced to differentiate into the adipocytic, chondrocytic, or osteocytic lineages (Pittenger et al., 1999, Science 284:143–147). Without wishing to be bound by theory, it appears that the stem cells giving rise to epithelial liver cell progenitors, myogenic progenitors, and/or bone, cartilage, fat, tendon, and marrow stromal cells is the KDR⁺ stem cell population of the present invention. Thus, the present invention provides methods of isolating and purifying cells which not only give rise to multilineage hematopoietic engraftment, but may also provide methods of targeting gene therapies to a wide variety of tissues including muscle and liver. Therefore, the prior art has only tantalized in suggesting that such multipotent cells existed, however, only the present invention teaches how to obtain them.

In summary, the major hurdle in studies on hematolymphopoietic stem cells (HSCS) has been the lack of an HSC-specific marker. The lack of a specific HSC marker hampered the purification, characterization and utilization of this extremely rare cell population. The data disclosed herein demonstrate, for the first time, that the vascular endothelial growth factor receptor 2 (VEGFR2, KDR/Flk-1) is a specific functional marker for human HSCs in adult bone marrow (BM), normal or mobilized peripheral blood (PB, MPB), and cord blood (CB). In these post-natal tissues, pluripotent repopulating HSCs are virtually restricted to and highly purified in the miniscule CD34⁺KDR⁺ cell fraction (<1% of CD34⁺ cells), as evaluated in NOD-SCID mice and fetal sheep xenografts. This CD34⁺KDR⁺ cell fraction contains essentially no oligo-unipotent hematopoietic progenitor cells (HPCs). Conversely, oligo-unipotent HPCs are virtually restricted to and highly purified in CD34⁺KDR⁻ cells, which contain essentially no HSCs.

In a representative experiment, the frequency of repopulating HSCs in the BM CD34⁺KDR⁺ subset, evaluated in NOD-SCID mice by limiting dilution assay (LDA), is 20%; similarly, representative experiments showed that the frequency of putative HSCs (CAFC) in the BM CD34⁺KDR⁺ subset, evaluated by LDA in 12-week extended Dexter-type long term culture (LTC), was 25%. The frequency rose in LTC supplemented with VEGF (to 53% in representative experiments), thus suggesting a functional role for the VEGF/KDR system in HSCs. Conversely, putative HSCs were essentially not detected in the CD34⁺KDR⁻ subset. In addition, the fraction of CD34⁺KDR⁺ cells resistant to prolonged GF starvation (except for VEGF addition) in FCS⁻ free culture comprises a very elevated frequency of putative HSCs, $\geq$80–95% in representative experiments.

The data disclosed herein indicate that KDR is a functional HSC defining marker, which distinguishes HSCs from oligo-unipotent HPCs. The present invention makes possible the characterization and functional manipulation of HSCs/HSC subsets, as well development of innovative approaches for HSC clinical utilization.

The disclosures of each and every patent, application and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of obtaning a cell population enriched for long-term repopulating human hematopoietic stem cells (HSCs), the method comprising isolating hematopoietic cells from a human hematopoietic tissue and separating cells that express KDR on their surface (KDR+ cells) from cells that do not express KDR on their surface using a reagent selected from the group consisting of
   i) an antibody that specifically binds with KDR,
   ii) a portion of an imrnunoglobilin, wherein the portion specifically binds with KDR, and
   iii) a conjugated vascular endothelial growth factor, thereby obtaining a KDR cell population that is enriched for long-term repopulating HSCS.

2. The method of claim 1, wherein the tissue is selected from the group consisting of an embryonic tissue, a fetal tissue, and a post-natal tissue.

3. The method of claim 1, wherein the tissue is an embryonic tissue selected from the group consisting of yolk sac and liver.

4. The method of claim 1, wherein the tissue is a fetal tissue selected from the group consisting of liver, bone marrow, and peripheral blood.

5. The method of claim 1, wherein the tissue is a post-natal tissue selected from the group consisting of cord blood, bone marrow, normal peripheral blood, mobilized peripheral blood, a hepatic tissue, and a splenic tissue.

6. The method of claim 1, wherein the reagent is an antibody.

7. The method of claim 6, wherein tile antibody is a monoclonal antibody.

8. The method of claim 7, wherein the monoclonal antibody is 260.4.

9. The method of claim 1, wherein the reagent is a conjugated vascular endothelial growth factor.

10. The method of claim 1, wherein the HSCs are starvation resistant long-term repopulating human HSCs.

11. A method of preparing long-term repopulating human HSCs, the method comprising isolating hematopoietic progenitor cells (BPCs) from a human hematopoietic tissue and separating HPCs that express KDR on their surface (KDR+ HPCs) from HPCs that do not express KDR on their surface using a reagent selected from the group consisting of
   i) an antibody that specifically binds with KDR,
   ii) a portion of an immunoglobulin, wherein the portion specifically binds with KDR, and
   iii) a conjugated vascular endothelial growth factor, whereby the isolated KDR+ HPCs are enriched for long-term repopulating HSCs.

12. The method of claim 11, wherein the tissue is selected from the group consisting of an embryonic tissue, a fetal tissue, and a post-natal tissue.

13. The method of claim 11, wherein the tissue is an embryonic tissue selected from the group consisting of yolk sac and liver.

14. The method of claim 11, wherein the tissue is a fetal tissue selected from the group consisting of liver, bone marrow, and peripheral blood.

15. The method of claim 11, wherein the tissue is a post-natal tissue selected from the group consisting of cord blood, bone marrow, normal peripheral blood, mobilized peripheral blood, a hepatic tissue, and a splenic tissue.

16. The method of claim 11, further comprising isolating KDR+ HPCs that do not express a late marker on their surface using an antibody specific for the late marker.

17. The method of claim 11, wherein the HPCs are isolated using an antibody that is specific for an early marker.

18. The method of claim 17, wherein the early marker is selected from the group consisting of CD34, Thy-1, c-kit receptor, flt3 receptor, AC133, vascular endothelial growth factor receptor I, vascular endothelial growth factor receptor III, Tie1, Tek, and basic fibroblast growth factor receptor.

19. The method of claim 18, wherein the early marker is CD34.

20. The method of claim 11, wherein the HPCs are isolated using a method selected from the group consisting of isolating a cell based on a physical property of the cell, and isolating a cell based on a biochemical/biological property.

21. The method of claim 11, further comprising isolating the long-term repopulating HSCs from other HPCs using one of an antibody that is specific for an early marker and an antibody that is specific for a late marker.

22. The method of claim 11, further comprising isolating the long-term repopulating HSCs from other HPCs using an antibody that is specific for a marker selected from the group consisting of CD34, Thy-1, c-kit receptor, flt3 receptor, AC133, vascular endothelial growth factor receptor I, vascular endothelial growth factor receptor III, Tie1, Tek, basic fibroblast growth factor receptor, CD2, CD3, CD4, CD7, CD8, CD15, CD16, CD19, CD20, CD33, CD38, CD45, CD56, CD71, and glycophorin A.

23. The method of claim 22, wherein the antibody is specific for CD34.

24. The method of claim 23, wherein the long-term repopulating HSCs are isolated from other HPCs using a second antibody that is specific for a one of a late marker and an early marker other than CD34.

25. The method of claim 22, wherein the long-term repopulating HSCs are isolated from other HPCs by selecting HPCs which express an early marker selected from the group consisting of CD34, Thy-1, c-kit receptor, flt3 receptor, AC133, vascular endothelial growth factor receptor 1, vascular endothelial growth factor receptor III, Tie1, Tek, and basic fibroblast growth factor receptor using an antibody that is specific for the early marker.

26. The method of claim 22, wherein the long-term repopulating HSCs are isolated from other HPCs by selecting HPCs which do not express a late marker selected from the group consisting of CD2, CD3, CD4, CD7, CD8, CD15, CD16, CD19, CD20, CD33, CD38, CD56, CD71, and glycophorin A using an antibody that is specific for the late marker.

27. The method of claim 11, wherein the HPCs are isolated from the tissue using an antibody which specifically binds CD34 to select CD34$^+$ HPCs.

28. The method of claim 27, wherein the KDR$^+$ HPCs are isolated from the CD34$^{30}$ HPCs using an antibody which specifically binds KDR.

29. The method of claim 28, wherein the antibody which specifically binds KDR is a polyclonal antibody.

30. The method of claim 28, wherein the antibody which specifically binds KDR is a monoclonal antibody.

31. The method of claim 30, wherein the monoclonal antibody is 260.4.

32. The method of claim 31, wherein the KDR$^+$ HPCs are starvation resistant.

33. A method of expanding long-term repopulating human HSCs, the method comprising isolating HSCs that express KDR on their surface (KDR$^+$ HSCs) from a human hematopoietic tissue using a reagent selected from the group consisting of i) an antibody that specifically binds with KDR,
ii) a portion of an immunoglobulin, wherein the portion specifically binds with KDR, and
iii) a conjugated vascular endothelial growth factor and incubating the HSCs with vascular endothelial growth factor to expand the HSCs.

34. The method of claim 33, further comprising incubating the population of HSCs with another growth factor.

35. The method of claim 34, wherein the other growth factor is selected from the group consisting of flt3 ligand, kit ligand, thrombopoietin, basic fibroblast growth factor, interleukin 6, interleukin 11, interleukin 3, granulomonocytic colony-stimulatory factor, granulocytic colony-stimulatory factor, monocytic colony-stimulatory factor, erythropoietin, angiopoietin, and hepatocyte growth factor.

36. A method of isolating a stem cell capable of giving rise to at least one of a muscle cell, a hepatic oval cell, a bone cell, a cartilage cell, a fat cell, a tendon cell, and a marrow stroma cell, the method comprising isolating a hematopoietic cell that expresses KDR on its surface from a human hematopoietic tissue using a reagent selected from the group consisting of i) an antibody that specifically binds with KDR,
ii) a portion of an immunoglobulin, wherein the portion specifically binds with KDR, and;
iii) a conjugated vascular endothelial growth factor, thereby isolating the stem cell.

37. The method of claim 36, wherein the tissue is selected from the group consisting of an embryonic tissue, a fetal tissue, and a post-natal tissue.

38. The method of claim 36, wherein the tissue is an embryonic tissue selected from the group consisting of yolk sac and liver.

39. The method of claim 36, wherein the tissue is a fetal tissue selected from the group consisting of liver, bone marrow, and peripheral blood.

40. The method of claim 36, wherein the tissue is a post-natal tissue selected from the group consisting of cord blood, bone marrow, normal peripheral blood, mobilized peripheral blood, a hepatic tissue, and a splenic tissue.

41. A method of obtaining a cell population enriched for long-term repopulating human hematopoietic stem cells (HSCs), the method comprising isolating hematopoietic cells from a human hematopoietic tissue and separating cells that express KDR on their surface but do not express a late marker on their surface from cells that either do not express KDR on their surface or express a late marker on their surface, the isolation method comprising using a reagent selected from the group consisting of i) an antibody that specifically binds with KDR,
ii) a portion of an immunoglobulin, wherein the portion specifically binds with KDR, and
iii) a conjugated vascular endothelial growth factor, thereby obtaining a cell population that is enriched for long-term repopulating HSCs.

42. A method of preparing long-term repopulating human HSCs, the method comprising isolating cells that express KDR On their surface and do not express a first early marker on their surface (KDR$^+$ early$^-$ cells) using, sequentially in either order, an antibody which specifically binds with the first early marker and a reagent selected from the group consisting of i) an antibody which specifically binds with KDR,
ii) a portion of an immunoglobulin, wherein the portion specifically binds with KDR, and
iii) a conjugated vascular endothelial growth factor.

43. The method of claim 42, further comprising isolating the long-term repopulating HSCs from the KDR$^+$ early$^-$ cells using an antibody which specifically binds one of a late marker and a second early marker.

44. The method of claim 42, further comprising isolating the long-term repopulating HSCs from the KDR$^+$ early$^-$ cells by isolating cells that do not express a late marker from the KDR$^+$ early$^-$ cells.

45. The method of claim 44, wherein the long-term repopulating HSCs are isolated using an antibody that binds specifically with a late marker selected from the group consisting of CD2, CD3, CD4, CD7, CD8, CD15, CD16, CD19, CD20, CD33, CD38, CD56, CD71, and glycophorin A.

46. The method of claim 44, comprising isolating KDR$^+$ early$^-$ cells that do not express any late marker of the group consisting of CD2, CD3, CD4, CD7, CD8, CD15, CD16, CD19, CD20, CD33, CD38, CD56, CD71, and glycophorin A from other KDR$^+$ early cells.

47. The method of claim 42, wherein the first early marker is CD34.

48. The method of claim 42, wherein the long-term repopulating human HSCs are prepared by isolating CD34$^-$ cells from the tissue using an antibody that binds specifically with CD34, and thereafter separating KDR$^+$ CD34$^-$ cells from other CD34$^-$ cells, whereby the KDR$^+$ CD34$^-$ cells are enriched for the HSCs.

49. The method of claim 42, further comprising separating CD34$^-$ cells that do not express a late marker (CD34late cells) selected from the group consisting of CD2, CD3, CD4, CD7, CD8, CD15, CD16, CD19, CD20, CD33, CD38, CD56, CD71, and glycophorin A on their surface from other CD34$^-$ cells, whereby the CD34$^-$late$^-$ cells are enriched for the HSCs.

50. The method of claim 49, wherein the separation of KDR⁺ and KDR⁻ CD34⁻ cells is performed prior to separating CD34⁻late⁻ cells from other CD34⁻ cells.

51. The method of claim 49, wherein the separation of KDR⁺ and KDR⁻ CD34⁻ cells is performed after separating CD34⁻late⁻ cells from other CD34⁻ cells.

52. The method of claim 42, wherein the reagent is an antibody.

53. The method of claim 42, wherein the reagent is a polyclonal antibody.

54. The method of claim 42, wherein the reagent is a monoclonal antibody.

55. The method of claim 54, wherein the monoclonal antibody is 260.4.

56. The method of claim 42, wherein CD34⁻ CD38⁻ cells are isolated from a human hematopoietic tissue.

57. The method of claim 56, further comprising isolating the long-term repopulating HSCs from other CD34⁻ CD38⁻ cells using an antibody which specifically binds on of a late marker other than CD38 and an early marker other than CD34.

58. The method of claim 42, wherein CD34⁻ cells that do not express a late marker are isolated from the tissue.

59. The method of claim 58, wherein the CD34⁻ cells do not express any late marker of the group consisting of CD2, CD3, CD4, CD7, CD8, CD15, CD16, CD19, CD20, CD33, CD38, CD56, CD71, and glycophorin A.

* * * * *